United States Patent [19]
Ashton et al.

[11] Patent Number: 5,801,165
[45] Date of Patent: Sep. 1, 1998

[54] ANTIINFLAMMATORY, IMMUNOSUPPRESSIVE AND ANTIALLERIC 16, 17-ALKYLIDIOXY-STEROIDS

[75] Inventors: Michael John Ashton; Sven Jan-Anders Karlsson; Bernard Yvon Jack Vacher; Michael Thomas Withnall, all of Dagenham, United Kingdom

[73] Assignee: Rhone-Poulenc Rorer Limited, West Malling, England

[21] Appl. No.: 459,954

[22] Filed: Jun. 2, 1995

Related U.S. Application Data

[63] Continuation of PCT/GB93/02659, Dec. 24, 1992.

[30] Foreign Application Priority Data

Dec. 24, 1992 [GB] United Kingdom ............ 9226917
Feb. 17, 1993 [GB] United Kingdom ............ 9303121

[51] Int. Cl.⁶ ............ C07J 71/00; C07J 75/00; A61K 31/58
[52] U.S. Cl. ............ 514/172; 514/174; 514/179; 514/180; 540/67; 552/525
[58] Field of Search ............ 540/67; 514/174, 514/179, 180, 172; 552/525

[56] References Cited

U.S. PATENT DOCUMENTS

| | | | |
|---|---|---|---|
| 3,198,792 | 8/1965 | Reerink et al. | |
| 4,361,559 | 11/1982 | Varma | |
| 4,404,200 | 9/1983 | Thalen et al. | 424/241 |
| 4,456,601 | 6/1984 | Toth et al. | 424/241 |
| 4,481,144 | 11/1984 | Varma | 260/397.45 |
| 4,499,021 | 2/1985 | Varma | 260/397.45 |
| 4,528,138 | 7/1985 | Varma et al. | 260/397.45 |
| 4,529,547 | 7/1985 | Varma | 260/397.3 |
| 4,868,169 | 9/1989 | O'Laughlin et al. | 514/179 |
| 4,868,170 | 9/1989 | Faustino et al. | 514/179 |
| 4,883,792 | 11/1989 | Timmins et al. | 514/169 |
| 4,933,168 | 6/1990 | Jones et al. | 514/174 |
| 4,950,659 | 8/1990 | Andersson et al. | 514/172 |

FOREIGN PATENT DOCUMENTS

| | | |
|---|---|---|
| 0 004 741 | 10/1979 | European Pat. Off. |
| 2 323 215 | 11/1973 | Germany |
| 2137206 | 10/1984 | United Kingdom |

OTHER PUBLICATIONS

1st Edition, MedPharm Sci. Pub., 1995, pp. 283–287, Mutschler, *Drugs Actions Basic Principles and Therapeutic Aspects*.

U.S. Application Serial No. 08/460479, dated Jun. 2, 1995, Ashton et al.

*Primary Examiner*—Kimberly J. Prior
*Attorney, Agent, or Firm*—Michael B. Martin; Raymond S. Parker, III; Paul R. Darkes

[57] ABSTRACT

Compounds of formula I

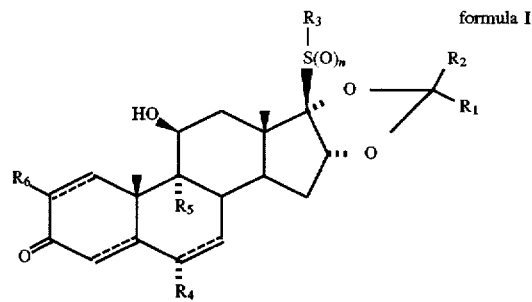

where $R_1$, $R_2$, $R_3$, $R_4$, $R_5$, $R_6$, n, and ═ are as defined herein, their use as antiinflammatory, immunosuppressive, and antiallergic agents, pharmaceutical compositions comprising them, and methods for their preparation comprising irradiating compounds of formula II

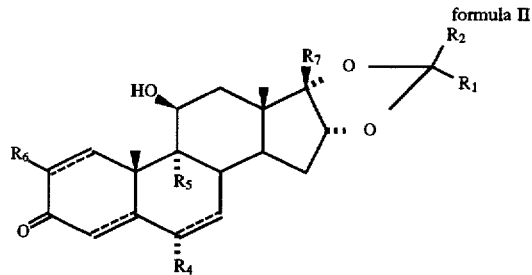

under an inert atmosphere, in the presence or absence of a compound of formula $R_3$—S—S(O)$_m$—$R_8$, where $R_7$, $R_8$, and m are as defined herein, and methods for their preparation comprising oxidizing, reducing, halogenating, or alkylating compounds of formula I are disclosed.

22 Claims, No Drawings

ANTIINFLAMMATORY, IMMUNOSUPPRESSIVE AND ANTIALLERIC 16,17-ALKYLIDIOXY-STEROIDS

BACKGROUND OF THE INVENTION

This application is a continuation-in-part application of PCT International Application Serial Number PCT/GB93/02659 having International filing date of Dec. 24, 1993, which application designates the United States as one of the Contracting States pursant to 35 U.S.C. Section 120 and which claims priority to Great Britain Applications 9226917.4 and 9303121.9 having filing dates of Dec. 24, 1992 and Feb. 17, 1993 respectively.

FIELD OF THE INVENTION

The present invention relates to novel antiinflammatory, immunosuppressive, and antiallergic compounds and to processes for their preparation. The invention also relates to pharmaceutical compositions containing the compounds. The invention also relates to the pharmacological uses of the compounds.

More particularly, this invention relates to new therapeutically useful steroids, processes for their preparation, pharmaceutical compositions containing them, and methods for their use, especially as anti-inflammatories.

The object of the invention is to provide a steroid which possesses high antiinflammatory, immunosuppressive and antiallergic activity, or a pharmaceutical composition thereof, with high activity at the site of application, e.g. in the respiratory tract, on the skin, in the joints, in the intestinal tract, or in the eye, coupled with low glucocorticoid systemic potency.

A large number of natural and synthetic steroids are known, and many of them are useful in the treatment of human and animal subjects. Steroids which have antiinflammatory properties are known, but they suffer from the disadvantage that, after administration, they cause unwanted side-effects outside the organ or tissue which is desired to be treated. It is well known that, in the pharmaceutical field and, in particular, in the field of steroids, small differences in chemical structure can produce compounds with completely different pharmacological activities. The present invention provides compounds which have never been described hitherto and which possess a remarkable combination of very useful antiinflammatory activity with a very low ability to produce undesired side-effects.

The nomenclature used in this application is as follows:

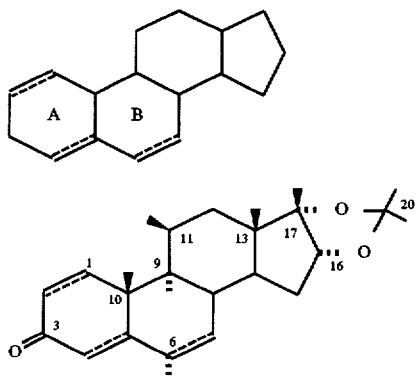

The 1,2-position and 4,5-position of the A ring and 6,7-position of the B ring may be saturated or a double bond.

The compounds of this invention may be described by general formula I

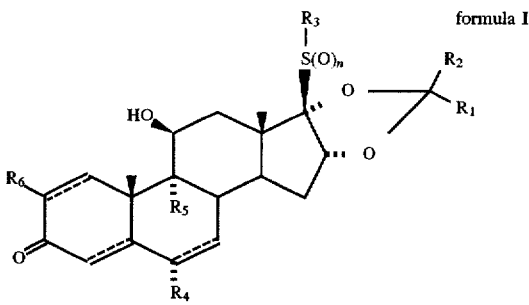

where:

$\equiv$ is independently at each of the 1,2-, 4,5- and 6,7-positions, a single or double bond;

$R_1$ is a straight- or branched-chain $C_{1-4}$ alkyl or $C_{2-4}$ alkenyl;

$R_2$ is hydrogen or methyl;

$R_3$ is $C_{1-7}$ alkyl, phenyl, substituted phenyl, heteroaryl, substituted heteroaryl or —$CH_2R$ where R is halo, hydroxy, $C_{1-5}$ alkoxy or $C_{1-10}$ alkanoyloxy;

$R_4$ is hydrogen, halo, hydroxy, keto or $C_{1-3}$ alkoxy when $\equiv$ at the 6,7-position forms a single bond, or hydrogen, halo or $C_{1-3}$ alkoxy when $\equiv$ at the 6,7-position forms a double bond;

$R_5$ is hydrogen or halo;

$R_6$ is hydrogen when $\equiv$ at the 1,2-position forms a single bond or hydrogen or chloro when $\equiv$ at the 1,2-position forms a double bond; and n is 0–2; and racemic mixtures and diastereoisomers thereof.

DETAILED DESCRIPTION AND PREFERRED EMBODIMENTS

The preferred compounds of this invention are described by formula I where:

$\equiv$ is a double bond at the 1,2- and 4,5-positions and a single bond at the 6,7-position or a double bond at the 4,5-position and single bonds at the 1,2- and 6,7-positions.

The more preferred compounds are described by formula I where:

$\equiv$ is a double bond at the 4,5-position and single bonds at the 1,2- and 6,7-positions;

$R_1$ is alkyl;

$R_2$ is hydrogen, or methyl;

$R_3$ is alkyl, haloalkyl or heteroaryl;

$R_4$ is hydrogen, halo, or keto;

$R_5$ is halo;

$R_6$ is hydrogen; and n is 0–2.

The most preferred compounds of this invention are described by formula I where:

$\equiv$ is a double bond at the 4,5-position and single bonds at the 1,2- and 6,7-positions;

$R_1$ is methyl, propyl or trans-prop-1-enyl;

$R_2$ is hydrogen, or methyl;

$R_3$ methyl, fluoromethyl or pyridyl;

$R_4$ is hydrogen, fluoro, or keto;

$R_5$ is fluoro;

$R_6$ is hydrogen; and n is 0–2.

An embodiment of this invention is described where the 1,2-, 4,5- and 6,7-positions are all single bonds.

Compounds of formula I can exist in two diastereoisomeric forms because two different configurations are possible at the carbon atom in the 20 position. As a result, the invention includes the (20R)- and (20S)-diastereo- isomers of the compounds of formula I, and mixtures thereof when $R_1$ and $R_2$ are different.

The preferred diastereoisomeric components are in the (20R)-configuration.

More specifically, the following compounds are within the scope of this invention:

9α-fluoro-11β-hydroxy-16α,17α-isopropylidenedioxy-17β-(methylthio)androsta-1,4-dien-3-one (20R,S)-16α,17α-butylidenedioxy-9α-fluoro-11β-hydroxy-17β-(methylthio)androsta-1,4-dien-3-one (20R)-16α,17α-butylidenedioxy-9α-fluoro-11β-hydroxy-17β-(methylthio)androsta-1,4-dien-3-one (20R,S)-16α,17α-butylidenedioxy-9α-fluoro-11β-hydroxy-17β-(2-pyridylthio)androsta-1,4-dien-3-one 9α-fluoro-11β-hydroxy-16α,17α-isopropylidenedioxy-17β-(methylsulphonyl)androsta-1,4-dien-3-one (20R,S)-16α,17α-butylidenedioxy-9α-fluoro-11β-hydroxy-17β-(methylsulphinyl)androsta-1,4-dien-3-one (20R)-16α,17α-butylidenedioxy-9β-fluoro-11β-hydroxy-17β-(methylsulphinyl)androsta-1,4-dien-3-one 6α,9α-difluoro-11β-hydroxy-16α,17α-isopropylidenedioxy-17β-(methylthio)androsta-1,4-dien-3-one (20R,S)-16α,17α-[(E)-2-butenylidenedioxy]-9α-fluoro-11β-hydroxy-17β-(methylthio)androsta-1,4-dien-3-one (20R)-16α,17α-[(E)-2-butenylidenedioxy]-9α-fluoro-11β-hydroxy-17β-(methylthio)androsta-1,4-dien-3-one (20R,S)-16α,17α-butylidenedioxy-9α-fluoro-11β-hydroxy-17β-(isopropylthio)androsta-1,4-dien-3-one (20R,S)-16α,17α-butylidenedioxy-17β-ethylthio-9α-fluoro-11β-hydroxyandrosta-1,4-dien-3-one (20R,S)-16α,17α-butylidenedioxy-9α-fluoro-11β-hydroxy-17β-(fluoromethylthio)androsta-1,4-dien-3-one (20R,S)-16α,17α-butylidenedioxy-6α,9α-difluoro-11β-hydroxy-17β-(methylthio)androsta-1,4-dien-3-one (20R)-16α,17α-butylidenedioxy-6α,9α-difluoro-11β-hydroxy-17β-(methylthio)androsta-1,4-dien-3-one (20S)-16α,17α-butylidenedioxy-6α,9α-difluoro-11β-hydroxy-17β-(methylthio)androsta-1,4-dien-3-one 9α-fluoro-11β-hydroxy-16α,17α-isopropylidenedioxy-17β(2-pyridylthio)androsta-1,4-dien-3-one hydrate (20R,S)-16α,17α-butylidenedioxy-6α,9α-difluoro-11β-hydroxy-17β-(methylsulphinyl)androsta-1,4-dien-3-one (20R)-16α,17α-butylidenedioxy-6α,9α-difluoro-11β-hydroxy-17β-(methylsulphinyl)androsta-1,4-dien-3-one 6α,9α-difluoro-11β-hydroxy-16α,17α-isopropylidenedioxy-17β-(fluoromethylthio)androsta-1,4-dien-3-one (20R,S)-16α,17α-butylidenedioxy-6α,9α-difluoro-11β-hydroxy-17β-(fluoromethylthio)androst-4-en-3-one (20R)-16α,17α-butylidenedioxy-6α,9α-difluoro-11β-hydroxy-17β-(fluoromethylthio)androst-4-en-3-one (20R,S)-16α,17α-butylidenedioxy-6α,9α-difluoro-11β-hydroxy-17β-(fluoromethylthio)androsta-1,4-dien-3-one (20R)-16α,17α-butylidenedioxy-6α,9α-difluoro-11β-hydroxy-17β-(fluoromethylthio)androsta-1,4-dien-3-one (20R,S)-16α,17α-butylidenedioxy-6α,9α-difluoro-11β-hydroxy-17β-(methylthio)androsta-1,4-dien-3-one (20S)-16α,17α-butylidenedioxy-6α,9α-difluoro-11β-hydroxy-17β-(methylthio)androsta-1,4-dien-3-one (20R,S)-16α,17α-butylidenedioxy-9α-fluoro-11β-hydroxy-17β-(methylthio)androst-4-en-3-one (20R,S)-16α,17α-butylidenedioxy-6α,9α-difluoro-11β-hydroxy-17β-(methylthio)androst-4-en-3-one (20R)-16α,17α-butylidenedioxy-6α,9α-difluoro-11β-hydroxy-17β-(methylthio)androst-4-en-3-one (20S)-16α,17α-butylidenedioxy-6α,9α-difluoro-11β-hydroxy-17β-(methylthio)androst-4-en-3-one (20R,S)-16α,17α-butylidenedioxy-9α-fluoro-11β-hydroxy-17β-(methylthio)androsta-1,4-diene-3,6-dione (20R)-16α,17α-butylidenedioxy-9α-fluoro-11β-hydroxy-17β-(methylthio)androsta-1,4-diene-3,6-dione (20R,S)-16α,17α-butylidenedioxy-6α,9αa-difluoro-11β-hydroxy-17β-(methylsulphonyl)androsta-1,4-dien-3-one (20R)-16α,17α-butylidenedioxy-6α,9α-difluoro-11β-hydroxy-17β-(methylsulphonyl)androsta-1,4-dien-3-one (20R,S)-16α,17α-butylidenedioxy-6α,9α-difluoro-11β-hydroxy-17β-(methylthio)androstan-3-one (20R)-16α,17α-butylidenedioxy-6α,9α-difluoro-11β-hydroxy-17β-(methylthio)androstan-3-one (20R,S)-6α,17α-butylidenedioxy-9α-fluoro-11β-hydroxy-17β-(methylthio)androst-4-ene-3,6-dione (20R)-16α,17α-butylidenedioxy-9α-fluoro-11β-hydroxy-17β-(methylthio)androst-4-ene-3,6-dione The compounds of this invention are extremely valuable in the local treatment of inflammatory, allergic and immunological diseases. These treatments include those currently treated by known steroids, such as diseases of the respiratory system, e.g. asthma and rhinitis, diseases of the skin, e.g. eczema, and diseases of the gastrointestinal tract, e.g. inflammatory bowel disease. However, because of the advantage of having little or no side effects, the compounds of this invention are much more desirable than previously known compounds.

The use of the compounds of formula I, and of pharmaceutical formulations containing them in the treatment of such diseases, form features of the present invention.

These utilities have been demonstrated in pharmacological tests which are believed to correlate well to activity in humans and other mammals.

The compounds of formula I can be prepared by the application or adaptation of known methods, by which is meant methods used hitherto or described in the literature.

The compounds of this invention may be prepared, for example, by the following reactions:

According to the present invention, compounds of formula I wherein n represents zero and ═, $R_1$, $R_2$, $R_3$, $R_4$, $R_5$ and $R_6$ are as hereinbefore defined, are prepared by a radical fragmentation reaction from compounds of formula II.

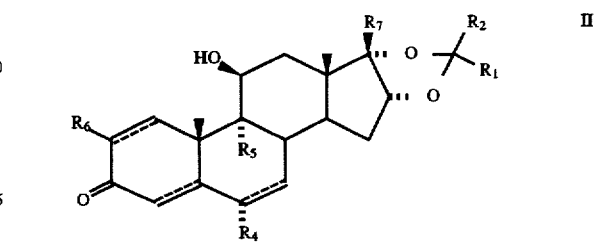

wherein ═, $R_1$, $R_2$, $R_4$, $R_5$ and $R_6$ are as hereinbefore defined, and $R_7$ represents a suitable group such as a 2-thioxo-1,2-dihydropyrid-1-yloxycarbonyl group, by irradiation in the presence of a compound of the general formula:

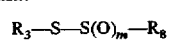

wherein $R_3$ is as hereinbefore defined, $R_8$ represents a hydrogen atom or an alkyl group containing up to about 7 carbon atoms, and m represents 0 or 2, under an inert atmosphere.

According to a further feature of the present invention, compounds of formula I wherein $R_3$ represents a pyridyl group, n represents zero, and $\underline{\phantom{...}}$, $R_1$, $R_2$, $R_4$, $R_5$ and $R_6$ are as hereinbefore defined, are prepared by a similar radical fragmentation reaction from compounds of formula II, hereinbefore depicted, wherein $\underline{\phantom{...}}$, $R_1$, $R_2$, $R_4$, $R_5$ and $R_6$ are as hereinbefore defined, and $R_7$ represents a 2-thioxo-1,2-dihydropyrid-1-yloxycarbonyl group, by irradiation in the absence of the said compounds of the general formula:

$$R_3-S-S(O)_m-R_8$$

According to a further feature of the invention, compounds of formula I can be prepared by the interconversion of other compounds of formula I.

For example, compounds of formula I wherein $\underline{\phantom{...}}$, $R_1$, $R_2$, $R_3$, $R_4$, $R_5$ and $R_6$ are as hereinbefore defined and n represents 1 or 2 are prepared by the oxidation of compounds of formula I wherein $\underline{\phantom{...}}$, $R_1$, $R_2$, $R_3$, $R_4$, $R_5$ and $R_6$ are as hereinbefore defined and n is less than in the desired product.

The oxidation may be performed by using a conventional oxidising agent such as potassium peroxymonosulphate to prepare products wherein n is 1 or a peracid to prepare products wherein n is 2.

As another example, compounds of formula I wherein $\underline{\phantom{...}}$, $R_1$, $R_2$, $R_4$, $R_5$ and $R_6$ are as hereinbefore defined, n represents zero, and $R_3$ represents a halomethyl group are prepared by the halogenation of compounds of formula I wherein $\underline{\phantom{...}}$, $R_1$, $R_2$, $R_4$, $R_5$ and $R_6$ are as hereinbefore defined, n represents zero, and $R_3$ represents a methyl group. For example, when $R_3$ represents a fluoromethyl group the reaction can be carried out by the action of xenon difluoride, preferably in the presence of an activated molecular sieve and a non-nucleophilic base.

As another example, compounds of formula I wherein $\underline{\phantom{...}}$, n, $R_1$, $R_2$, $R_3$, $R_5$ and $R_6$ are as hereinbefore defined, and $R_4$ represents an alkoxy group are prepared by the alkylation of compounds of formula I wherein $\underline{\phantom{...}}$, n, $R_1$, $R_2$, $R_3$, $R_5$ and $R_6$ are as hereinbefore defined, and $R_4$ represents a hydroxy group, by known methods, for example by reaction with a base followed by reaction with an alkyl halide, e.g. methyl iodide when $R_4$ is methoxy.

As another example, compounds of formula I wherein one or more of the symbols $\underline{\phantom{...}}$, forms a single bond, the symbols otherwise being as hereinbefore defined, are prepared from compounds of formula I wherein said symbol or symbols $\underline{\phantom{...}}$ form double bonds by hydrogenation in the presence of a catalyst. For example compounds of formula I wherein the symbol $\underline{\phantom{...}}$, forms a single bond in the 1,2-position, the symbols otherwise being as hereinbefore defined, are prepared from compounds of formula I wherein said symbol $\underline{\phantom{...}}$ forms a double bond by hydrogenation in the presence of a rhodium compound, e.g. rhodium tris(triphenylphosphine) chloride.

The diastereoisomers of general formula I can be separated from their mixtures, by the application or adaptation of known methods, for example chromatographic and recrystallisation techniques, or they may be separately prepared from the appropriate isomers of their intermediates, for example by the application or adaptation of methods described herein.

The starting materials and intermediates can be prepared by the application or adaptation of known methods, for example methods described in the Reference Examples or their obvious chemical equivalents.

For example, compounds of formula II can be prepared from compounds of formula III,

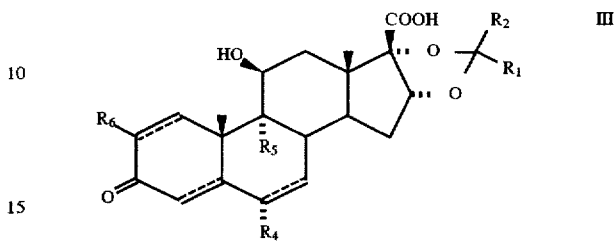

wherein $\underline{\phantom{...}}$, $R_1$, $R_2$, $R_4$, $R_5$ and $R_6$ are as hereinbefore defined, by conversion of the carboxy group to the said group $R_7$, by the application or adaptation of known methods.

Compounds of formula III can be prepared from compounds of the general formula IV,

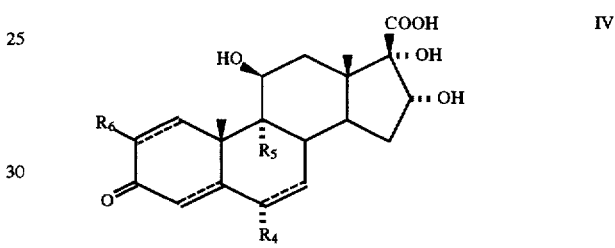

wherein $\underline{\phantom{...}}$, $R_4$, $R_5$ and $R_6$ are as hereinbefore defined, by reaction with compounds of the general formula:

$$R_1R_2CO \text{ or } R_1R_2C(OR_9)_2$$

wherein $R_1$ and $R_2$ are as hereinbefore defined and $R_9$ is a methyl or ethyl group, in the presence of a protic acid, e.g. perchloric acid.

Compounds of formula IV wherein $R_4$ represents a hydroxy group and $\underline{\phantom{...}}$, $R_5$ and $R_6$ are as hereinbefore defined, can be prepared from compounds of the general formula V,

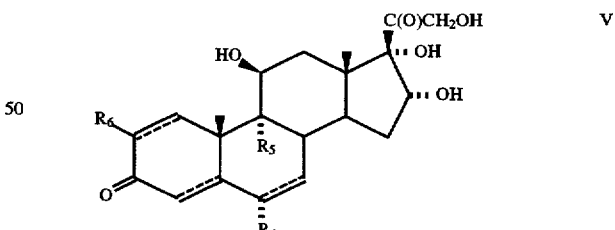

wherein $\underline{\phantom{...}}$, $R_5$ and $R_6$ are as hereinbefore defined, by reaction with potassium superoxide in the presence of an agent such as 1,4,7,10,13,16-hexaoxa-cyclooctadecane, preferably in a solvent such as dimethylformamide.

Alternatively, compounds of formula III can be prepared by the following reaction sequence.

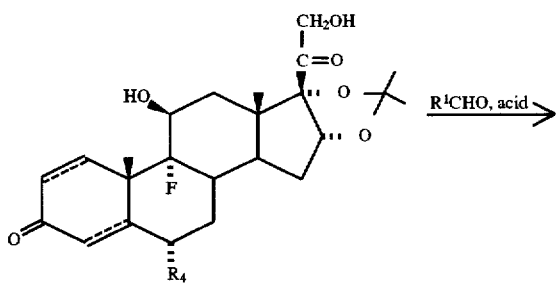

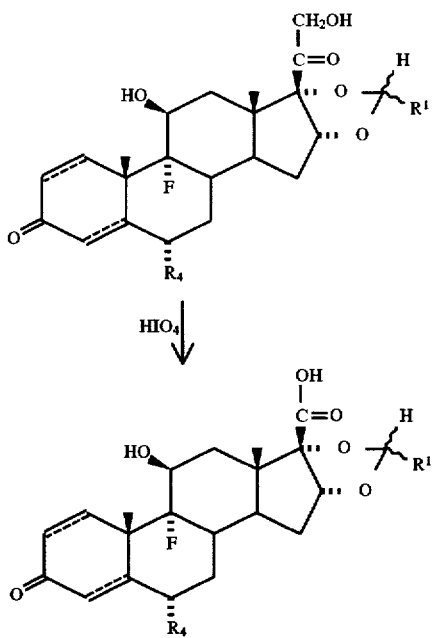

METHODS OF PREPARATION

The following Examples illustrate the preparation of compounds according to the present invention. All $^1$H-NMR spectra are recorded at 400 MHz. The chemical shifts are expressed in ppm relative to tetramethylsilane. Abbreviation in the text have the following significances: s=singlet, d=doublet, t=triplet, q=quartet, dd=doublet of doublets, dt=doublet of triplets, m=multiplet, c=unresolved complex peak, b=broad signal. Optical rotations are measured using a polarimeter model AA-10.

EXAMPLE 1

1.1) 9α-Fluoro-11β-hydroxy-16α,17α-isopropylidenedioxy-17β-(methylthio)androsta-1,4-dien-3-one A solution of 9α-fluoro-11β-hydroxy-16α,17α-isopropylidenedioxy-17β-(2-thiop yridone-1-oxycarbonyl)androsta-1,4-dien-3-one (2.1 g) in dimethyl disulfide (80 ml) is irradiated with a tungsten lamp (300 W) at −8° C. under an atmosphere of nitrogen untill the reaction is complete (1–3 hours). The dimethyl disulfide is removed under vacuo and the residue purified by low pressure liquid chromatography on silica gel eluting with chloroform. The solid obtained after evaporation of the solvent is recrystallised from ethyl acetate to give 9α-fluoro-11β-hydroxy-16α,17α-isopropylidenedioxy-17β-(methylthio)androsta-1,4-dien-3-one as a white solid (0.5 g, 1.2 mmol), m.p. 256° C.; [N.M.R. (DMSO, d6): 1.13 (s, 3H), 1.27–1.39 (m,1H), 1.33 (s, 3H), 1.44 (dd, 1H), 1.50 (s, 3H), 1.54 (s, 3H), 1.59 (dt, 1H), 1.68 (d, 1H), 1.81 (c, 1H), 1.93–2.03 (m, 2H), 2.11 (s, 3H), 2.35 (dt, 1H), 2.4 (m, 1H), 2.63 (dt, 1H), 4.13 (c, 1H), 4.39 (d, 1H), 5.34 (c, 1H), 6.01 (s 1H), 6.23 (dd, 1H), 7.28 (d,1H); Found: C, 65.3; H, 7.5% Calculated for $C_{23}H_{31}FO_4S$: C, 65.4; H, 7.4%].

1.2) (20R)-16α,17α-Butylidenedioxy-9α-fluoro-11β-hydroxy-17β-(methylthio)androsta-1,4-dien-3-one A solution of 2-thioxo-1,2-dihydropyrid-1-yl (20R,S)-3-oxo-9α-fluoro-11β-hydroxy-16α,17α-butylidenedioxyandrosta-1,4-diene-17β-carboxylate (2 g) in dimethyl formamide (5 ml) and dimethyl disulfide (75 ml) is treated as described above. After work up, the powder obtained is recrystallised from ethyl acetate to give (20R)-16α,17α-butylidenedioxy-9α-fluoro-11β-hydroxy-17β-(methylthio)androsta-1,4-dien-3-one (0.63 g, 1.44 mmol) as a white solid in a stereoisomeric purity greater than 98%, m.p. 187° C.; [N.M.R. (DMSO, d6): 0.87 (t, 3H), 1.18 (s, 3H), 1.23–1.61 (m, 7H), 1.50 (s, 3H), 1.61 (d, 1H), 1.80 (m, 1H), 1.93–2.05 (m, 2H), 2.09 (s, 3H), 2.33 (dd, 1H), 2.4 (m, 1H), 2.64 (dt, 1H), 4.12 (c, 1H), 4.14 (d, 1H), 5.13 (t, 1H), 5.35 (c, 1H), 6.02 (s, 1H), 6.23 (dd, 1H), 7.28 (d, 1H); Found: C, 65.8; H, 7.6% Calculated for $C_{24}H_{33}FO_4S$: C, 66.0 H, 7.6%].

1.3) (20R)-16α,17α-Butylidenedioxy-6α,9α-difluoro-11β-hydroxy-17β-(methylthio)androsta-1,4-dien-3-one (20S)-16α,17α-Butylidenedioxy-6α,9α-difluoro-11β-hydroxy-17β-(methylthio)androsta-1,4-dien-3-one 2-Thioxo-1,2-dihydropyrid-1-yl (20R,S)-3-oxo-6α,9α-difluoro-11β-hydroxy-16α,17α-butylidenedioxyandrosta-1,4-diene-17β-carboxylate (19.5 g) is dissolved in dichloromethane (40 ml) and dimethyl disulfide (430 ml) and is irradiated as described above. The reaction mixture is concentrated in vacuo, the residue is taken up in ethyl acetate (400 ml) and washed successively with hydrochloric acid (1N, two times 200 ml), water (200 ml) and brine (two times 200 ml). The ethyl acetate phase is dried over sodium sulfate, and filtration of the dessicant and concentration in vacuo gives a pale yellow foam (13.1 g) from which the mixture of epimers (20R,S)-in proportion of 80% to 20% is resolved by preparative HPLC using a Dynamax RP-18 column and methanol/water as mobile phase. (20R)-16α,17α-butylidenedioxy-6α,9α-difluoro-11β-hydroxy-17β-(methylthio)-androsta-1,4-dien-3-one is obtained as a white solid (6.55 g, 14.4 mmol), m.p. 204°–6° C.; [a]26=+108o, c=0.067 (CH3CN); [N.M.R. (DMSO, d6): 0.87 (t, 3H), 1.16 (s, 3H), 1.33–1.43 (m, 3H), 1.43–1.54 (m, 1H), 1.50 (s, 3H), 1.54–1.63 (m, 3H), 1.73 (d, 1H), 1.97–2.08 (m, 2H), 2.10 (s, 3H), 2.26 (c, 1H), 2.48–2.63 (m, 1H), 4.14 (c, 1H), 4.16 (d, 1H), 5.12 (t, 1H), 5.43 (c, 1H), 5.63 (m, 1H), 6.11 (s, 1H), 6.30 (dd, 1H), 7.26 (dd,1H); Found: C, 63.4; H, 7.3% Calculated for $C_{24}H_{32}F_2O_4S$: C, 63.4; H, 7.1%], and (20S)-6α,9α-difluoro-11β-hydroxy-16α,17α-butylidenedioxy- 17β-methylthioandrosta-1,4-dien-3-one is obtained as a white solid (0.6 g), m.p. 198°–9° C.; [N.M.R. (DMSO, d6): 0.87 (t,3H), 1.08 (s, 3H), 1.3–1.4 (m, 3H), 1.49 (s, 3H), 1.5–1.65 (m, 3H), 1.59 (d, 1H), 1.75–1.9 (m, 2H), 1.95 (dt, 1H), 2.05 (s, 3H), 2.25 (c, 1H), 2.4–2.51 (m, 1H), 4.1–4.2 (c, 1H), 4.78 (d, 1H), 5.11 (t, 1H), 5.44 (c, 1H), 5.63 (m, 1H), 6.1 (s, 1H), 6.28 (dd, 1H), 7.25 (dd, 1H); Found: C, 63.9; H, 7.2% Calculated for $C_{24}H_{32}F_2O_4S$: C, 63.4; H, 7.1%]

1.4) (20R)-16α,17α-[(E)-2-Butenylidenedioxy]-9α-fluoro-11β-hydroxy-17β-(methylthio)androsta-1,4-dien-3-one In an analogous manner 2-thioxo-1,2-dihydropyrid-1-yl (20R,S)-3-oxo-9α-fluoro-11β-hydroxy-16α,17α-(E)-[but-2-enylidenedioxy]androsta-1,4-diene-17β-carboxylate (1.85 g) as starting material gives after recrystallisation in diethyl ether (20R)-16α,17α-[(E)-2-butenylidenedioxy]-9α-fluoro-11β-hydroxy-17β-(methylthio)androsta-1,4-dien-3-one as a white solid (0.25 g, 0.57 mmol) in a stereoisomeric purity greater than 96%, m.p. 204°–6° C.; [N.M.R. (DMSO, d6): 1.17 (s, 3H), 1.33 (m, 1H), 1.44 (dd, 1H), 1.50 (s, 3H), 1.57 (dt, 1H), 1.69 (dd, 3H), 1.71 (d, 1H), 1.80 (m, 1H), 1.92–2.04 (m, 2H), 2.10 (s, 3H), 2.33 (dd, 1H), 2.30–2.50 (m, 1H), 2.63 (dt, 1H), 4.11 (c, 1H), 4.18 (d, 1H), 5.35 (c, 1H), 5.37–5.45 (m, 2H), 5.96 (m, 1H), 6.02 (s, 1H), 6.24 (dd, 1H), 7.28 (d, 1H); Found: C, 66.5; H, 7.30% Calculated for $C_{24}H_{31}FO_4S$: C, 66.33; H, 7.19%].

1.5) 6α,9α-Difluoro-11β-hydroxy-16α,17α-isopropylidenedioxy-17β-(methylthio)androsta-1,4-dien-3-one In an analogous manner 2-thioxo-1,2-dihydropyrid-1-yl 3-oxo-6α,9α-difluoro-11β-hydroxy-16α,17α-isopropylidenedioxyandrosta-1,4-diene-17β-carboxylate (2.5 g) gives after purification by low pressure liquid chromatography on silica gel eluting with a mixture of dichloromethane (95%) and methanol (5%) followed by recrysallisation of the white solid obtained from acetonitrile 6α,9α-difluoro-11β-hydroxy-16α,17α-isopropylidenedioxy-17β-(methylthio)androsta-1,4-dien-3-one (0.46 g, 1.0 mmol), m.p. 255°–6° C.; [N.M.R. (DMSO, d6): 1.13 (s,3H), 1.33 (s, 3H), 1.45 (m, 2H), 1.50 (s, 3H), 1.55 (s, 3H), 1.64 (dd, 1 H), 1.70 (d,1H), 1.96–2.09 (m, 2H), 2.12 (s, 3H), 2.26 (m, 1H), 2.45–2.62 (m, 1H), 4.13 (c, 1H), 4.42 (d, 1H), 5.41 (c, 1H), 5.63 (m, 1H), 6.10 (s, 1H), 6.29 (dd, 1H), 7.25 (dd, 1H); Found: C, 62.6; H, 6.92% Calculated for $C_{23}H_{30}F_2O_4S$: C, 62.71; H, 6.86%].

EXAMPLE 2

2.1) (20R,S)-16α,17α-Butylidenedioxy-17β-ethylthio-9α-fluoro-11β-hydroxyandrosta-1,4-dien-3-one 2-Thioxo-1,2-dihydropyrid-1-yl (20R,S)-3-oxo-9α-fluoro-11β-hydroxy-16α,17α-butylidenedioxyandrosta-1,4-diene-17β-carboxylate (1 g) dissolved in dimethyl formamide (5 ml) and diethyl disulfide (35 ml) is irradiated at –40° C. for 3 hours under a nitrogen atmosphere. The solvents are removed in vacuo (70° C., 0.4 mmHg) and the residue purified by low pressure liquid chromatography on silica gel eluting with chloroform. The solid obtained after evaporation of the solvent is recrystallised from a mixture of ethyl acetate and hexane to give (20R,S)-16α,17α-butylidenedioxy-17β-ethylthio-9α-fluoro- 11β-hydroxyandrosta-1,4-dien-3-one as a white solid (0.30 g, 0.66 mmol) in an epimeric proportion of 85/15%, m.p. 228°–9° C.; [N.M.R. (DMSO, d6): 0.87 (t, 2.55H), 0.89 (t, 0.45H), 1.07 (s, 0.45H), 1.17 (m, 5.55H), 1.27–1.46 (m, 4H), 1.49 (s, 0.45H), 1.50 (s, 2.55H), 1.50–1.60 (m, 3H), 1.73 (d, 1H), 1.80 (m, 1H), 1.95 (dt, 1H), 2.02 (dt,1H), 2.33 (dd, 1H), 2.33–2.47 (m, 1 H), 2.64 (dt,1 H), 2.68 (q, 2H), 4.11 (d, 0.85H), 4.13 (c, 1H), 4.75 (d, 0.15H), 5.07 (t, 0.15H), 5.16 (t, 0.85H), 5.33 (c,085H), 5.38 (c, 0.15H), 6.0 (s, 1H), 6.22 (dd, 1H), 7.28 (d, 1H); Found: C, 66.3; H, 7.90% Calculated for $C_{25}H_{35}FO_4S$: C, 66.6; H, 7.80%].

2.2) (20R,S)-16α,17α-Butylidenedioxy-9α-fluoro-11β-hydroxy-17β-(isopropylthio)androsta-1,4-dien-3-one 2-Thioxo-1,2-dihydropyrid-1-yl (20R,S)-3-oxo-9α-fluoro-11β-hydroxy-16α,17α-butylidenedioxyandrosta-1,4-diene-17β-carboxylate (2.40 g) dissolved in dimethyl formamide (10 ml) and diisopropyl disulfide (40 ml) is treated as described above. Recrystallisation from a mixture of ethyl acetate and petroleum spirit gives (20R,S)-9α-fluoro-11β-hydroxy-16α,17α-butylidenedioxy-17β-isopropylthio-androsta-1,4-dien-3-one as a white solid (0.60 g, 1.29 mmol) in an epimeric proportion of 85/15%, m.p. 235° C.; [N.M.R. (DMSO, d6): 0.88 (t, 2.55H), 0.92 (t, 0.45H), 1.05 (s, 0.45H), 1.17 (s, 2.55H), 1.23 (d, 3H), 1.28 (d, 3H), 1.30–1.45 (m, 4H), 1.49 (s, 0.45H), 1.50 (s, 2.55H), 1.50–1.63 (m, 3H), 1.67–1.84 (m, 2H), 1.95 (dt,1H), 2.07 (dt, 1H), 2.32 (dd, 1H), 2.35–2.50 (m 1H), 2.63 (dt, 1H), 3.42 (m, 1H), 4.08 (d, 0.85H), 4.15 (c, 1H),4.73 (d, 0.15H), 5.08 (t, 0.15H), 5.16 (t, 0.85H), 5.37 (c, 1H), 6.02 (s, 1H), 6.23 (dd, 1H), 7.28 (d, 1H); Found: C, 66.6; H, 8.10% Calculated for $C_{26}H_{37}FO_4S$: C, 67.2; H, 8.00%].

EXAMPLE 3

3.1) 6α,9α-Difluoro-11β-hydroxy-16α,17α-isopropylidenedioxy-17β-(fluoromethylthio)androsta-1,4-dien-3-one A mixture of 6α,9α-difluoro-11β-hydroxy-16α,17α-isopropylidenedioxy-17β-methylthio-androsta-1,4-dien-3-one (5.06 g, 11.5 mmol), 2,6-di-t-butyl-4-methylpyridine (5.19 g, 25.3 mmol) and activated molecular sieve (type 4 A, 7.5 g) in dry dichloromethane (250 ml) is stirred for 1.5 hours under an argon atmosphere at 20° C. Xenon difluoride (2.15 g, 12.7 mmol) is added in one portion and the mixture stirred at 20° C. for 3 hours. After the molecular sieve is filtered off, the homogeneous solution is poured into ice cold water (500 ml), decanted and the aqueous phase extracted with dichloromethane (200 ml). The combined organic phases are washed with brine (100 ml) and concentrated in vacuo. The residue is taken up in ethyl acetate (500 ml), washed with hydrochloric acid (1N, three times 250 ml), water (250 ml), brine (250 ml) and then the organic phase is dried over magnesium sulfate. Filtration of the dessicant and concentration in vacuo gives a white solid (3.6 g) which is purified by preparative HPLC using a Dynamax RP-18 column and methanol/water as mobile phase. 6α,9α-difluoro-11β-hydroxy-16α,17α-isopropylidenedioxy-17β-(fluoromethylthio)androsta-1,4-dien-3-one (2.4 g, 5.23 mmol) is obtained as a white solid which is recrystallised from acetonitrile, m.p. 268°–9° C.; $[α]^{26}$ =+162°, c=0.057 (CH3CN); [N.M.R. (DMSO, d6): 1.06 (s, 3H), 1.36 (s, 3H), 1.45 (s, 3H), 1.46–1.57 (m, 2H), 1.50 (s, 3H), 1.69 (dt, 1H), 1.73 (d, 1H), 1.82 (dt, 1H), 2.05 (dt, 1H), 2.29 (c, 1H), 2.47–2.63 (m, 1H), 4.15 (c, 1H), 4.63 (d, 1H), 5.52 (c, 1H), 5.62 (m, 1H), 5.65 (dd, 1H), 5.79 (dd, 1H), 6.10 (s, 1H), 6.29 (dd, 1H), 7.25 (dd, 1H); Found: C, 60.2; H, 6.37% Calculated for $C_{23}H_{29}F_3O_4S$: C, 60.25; H, 6.37%].

3.2) (20R)-16α,17α-Butylidenedioxy-9α-fluoro-11β-hydroxy-17β-(fluoromethylthio)androsta-1,4-dien-3-one (20R)-9α-Fluoro-11β-hydroxy-16α,17α-butylidenedioxy-17β-methylthio-androsta-1,4-dien-3-one (2.0 g, 4.58 mmol) is treated with 2,6-di-t-butyl-4-methylpyridine (2.05 g, 10 mmol) and xenon difluoride (0.85 g, 5.0 mmol) in dichloromethane (100 ml) as described above. After work up, the residue is purified by low pressure liquid chromatography on silica gel eluting with chloroform and the white solid obtained (0.6 g) recrystallised from a mixture of ethyl acetate and petroleum spirit to give (20R)-16α,17α- butylidenedioxy-9α-fluoro-11β-hydroxy-17β-(fluoromethylthio)androsta-1,4-dien-3-one (0.25 g, 0.55 mmol), m.p. 160° C. (dec.); [N.M.R. (DMSO, d6): 0.87 (t, 3H), 1.09 (s, 3H), 1.26–1.41 (m, 3H), 1.44–1.50 (m, 1H), 1.50 (s, 3H), 1.54–1.64 (m, 3H), 1.73 (d, 1H), 1.78–2.0 (m, 3H), 2.33 (dd, 1H), 2.35–2.50 (m, 1H), 2.62 (dt, 1H), 4.17 (c, 1H), 4.38 (d, 1H), 5.09 (t, 1H), 5.45 (c, 1H), 5.59 (dd, 1H), 5.72 (dd, 1H), 6.01 (s, 1H), 6.22 (dd, 1H), 7.28 (d, 1H); Found: C, 63.4; H, 7.10% Calculated for $C_{24}H_{32}F_2O_4S$: C, 63.4, H, 7.10%].

3.3) (20R)-16α,17α-Butylidenedioxy-6α,9α-difluoro-11β-hydroxy-17β-(fluoromethylthio)androsta-1,4-dien-3-one (20R)-6α,9α-Difluoro-11β-hydroxy-16α,17α-butylidenedioxy-17β-methylthio-androsta-1,4-dien-3-one (1.7 g, 3.5 mmol) is treated with 2,6-di-t-butyl-4-methyl-pyridine (1.57 g, 7.66 mmol) and xenon difluoride (0.65 g, 3.8 mmol) in dichloromethane (100 ml) as described above. After work up, the white powder obtained (1.3 g) is purified by low pressure liquid chromatography on silica gel eluting with chloroform to give (20R)-16α,17α-butylidenedioxy-6α,9α-difluoro-11β-hydroxy-17β-(fluoromethylthio) androsta-1,4-dien-3-one as a white solid (0.32 g, 0.68 mmol), m.p. 145°-6° C.; [N.M.R. (DMSO, d6): 0.88 (t, 3H), 1.08 (s, 3H), 1.31–1.50 (m, 3H), 1.50 (s, 3H), 1.50–1.55 (m, 1H), 1.53–1.68 (m, 3H), 1.75 (d, 1H), 1.89 (dt, 1H), 2.03 (dt, 1H), 2.27 (c, 1H), 2.50–2.66 (m, 1H), 4.17 (c, 1H), 4.40 (d, 1H), 5.09 (t, 1H), 5.53–5.10 (m, 1.5H), 5.58 (dd, 1H), 5.65–5.74 (m, 0.5H), 5.73 (dd, 1H), 6.11 (s, 1H), 6.30 (dd, 1H), 7.24 (dd, 1H); Found: C, 61.2; H, 6.70% Calculated for $C_{24}H_{31}F_3O_4S$: C, 60.99; H, 6.60%].

EXAMPLE 4

4.1) (20R,S)-16α,17α-Butylidenedioxy-9α-fluoro-11β-hydroxy-17β-(2-pyridylthio)androsta-1,4-dien-3-one 2-Thioxo-1,2-dihydropyrid-1-yl (20R,S)-3-oxo-9α-fluoro-11β-hydroxy-16α,17α-butylidenedioxyandrosta-1,4-diene-17β-carboxylate (0.60 g) dissolved in dichloromethane (50 ml) is irradiated under a nitrogen atmosphere as described above. The temperature is maintained at 20° C. by external cooling and irradiation continued untill the reaction mixture became colourless (45 minutes). The reaction mixture is concentrated in vacuo and the product isolated by low pressure liquid chromatography on silica gel eluting with chloroform. Recrystallisation from a mixture of ethyl acetate and petroleum spirit gives (20R,S)-16α,17α-butylidenedioxy-9α-fluoro-11β-hydroxy-17β-(2-pyridylthio)-androsta-1,4-dien-3-one as a white solid (0.15 g, 0.30 mmol) in an epimeric proportion of 85/15%, m.p. 215° C.; N.M.R. (DMSO, d6): 0.75 (t, 0.45H), 0.88 (t, 2.55H), 1.17 (m, 1H), 1.20 (s, 3H), 1.22–1.45 (m, 3H), 1.46 (s, 3H), 1.45–1.55 (m, 2H), 1.56–1.69 (m, 2H), 1.82 (m, 2H), 1.94 (dt, 1H), 2.33 (dd, 1H), 2.40 (m, 1H), 2.62 (dt, 1H), 3.98 (c, 1H), 4.45 (d, 0.85H), 5.03 (d, 0.15H), 5.10 (t, 0.15H), 5.22 (t, 0.85H), 5.31 (c, 0.85H), 5.38 (c, 0.15H), 6.0 (s, 1H), 6.19 (dd, 0.85H), 6.21 (dd, 0.15H), 7.20 (d, 0.85H), 7.25 (d, 0.15H), 7.29 (dt, 1H), 7.66 (dd, 1H), 8.21 (dt, 1H), 8.48 (ddd, 1H); Found: C, 67.0; H, 6.87; N, 2.70% Calculated for C28H34FNO4S: C, 67.30; H, 6.80; N, 2.80%].

4.2) 9α-Fluoro-11β-hydroxy-16α,17α-isopropylidenedioxy-17β-(2-pyridylthio)androsta-1,4-dien-3-one By proceeding in a similar manner 2-thioxo-1,2-dihydropyrid-1-yl 9α-fluoro-11β-hydroxy-16α,17α-isopropylidenedioxy-3-oxoandrosta-1,4-diene-17β-carboxylate (9g) gives after work up a white solid (2.9 g) . Recrystalisation from diethyl ether gives 9α-fluoro-11β-hydroxy-16α,17α-isopropylidenedioxy-17β-(2-pyridylthio)androsta-1,4-dien-3-one hydrate as a yellow solid (0.63 g).

m.p. 183°-6° C.; [N.M.R. (DMSO, d6): 1.14–1.22 (m, 4H), 1.25–1.42 (m, 1H), 1.38 (s, 3H), 1.47 (s, 3H), 1.47–1.55 (m,1 H), 1.59 (s, 3H), 1.62–1.75 (m,1H), 1.78–1.92 (m, 2H), 1.93–2.05 (m, 1H), 2.29–2.48 (m, 2H), 2.55–2.67 (m,1H), 3.98 (c, 1H), 4.69(d, 1H), 5.29 (c, 1H), 6.0 (s, 1H), 6.19 (dd, 1H), 7.2 (d, 1H), 7.24 (m, 1H), 7.67–7.75 (m, 2H), 8.45 (m, 1H); Found: C, 64.1; H, 6.49; N 2.50% Calculated for $C_{27}H_{32}FNO_4S.H_2O$: C, 64.39; H, 6.40; N, 2.78%].

EXAMPLE 5

5.1) (20R,S)-16α,17α-Butylidenedioxy-9α-fluoro-11β-hydroxy-17β-(methylthio)androsta-1,4-diene-3,6-dione Irradiation of 2-thioxo-1,2-dihydropyrid-1-yl (20R,S)-3,6-dioxo-9α-fluoro-11β-hydroxy-16α,17α-butylidenedioxyandrosta-1,4-diene-17β-carboxylate (1.83g, 3.28mmol) in the presence of dimethyl disulfide according to the procedures described above gives a pale cream solid (1.36 g) which is recrystallized from diethyl ether to give an off-white solid (1.1 g) which is recrystallized a second time from acetonitrile to afford (20R,S)-16α,17α-butylidenedioxy-9α-fluoro-11β-hydroxy-17β-(methylthio)androsta-1,4-diene-3,6-dione as a white solid (0.33g, 0.73mmol) in a diastereoisomeric purity greater than 95%, m.p. 241°–243° C.; [NMR(DMSO,d6): 0.88(t,3H), 1.19(s, 3H), 1.33–1.47(m,3H), 1.49(s,3H), 1.55–1.64(m,3H), 1.82 (d,1H), 2.07(m,2H), 2.10 (s,3H), 2.29(dd,1H), 2.73(dd,1H), 2.73–2.95(m,1H), 4.17(d,1H), 4.23(c,1H), 5.13 (t,1H), 5.61 (c,1H), 6.29(d, 1H), 6.40(dd,1H), 7.43(d,1H); Found: C,64.0;H,7.00%. Calculated for $C_{24}H_{31}FO_5S$: C,64.0:H, 6.93%].

EXAMPLE 6

6.1) (20R,S)-16α,17α-Butylidenedioxy-6α,9α-difluoro-11β-hydroxy-3-oxoandrost-4-ene-17β-carboxylic acid To a degassed ($N_2$) solution of methanol (250 ml) and water (15 ml) is added sodium hydroxide pellets (5.52 g,138 mmol). When homogeneous, (20R,S)-16α,17α-butylidenedioxy-6α,9α-difluoro-11β-hydroxy-3-oxoandrosta-1,4-diene-17β-carboxylic acid (12.48 g,27.6 mmol) is added in one portion and the suspension stirred until a yellow solution is obtained. The reaction mixture is treated dropwise at room temperature with iron pentacarbonyl (36.31 ml,276 mmol), then heated at 50° C. for 20 hours under an atmosphere of nitrogen. The cooled reaction mixture is poured into an ice-cold aqueous solution of sulfuric acid (4N,1000 ml), dichloromethane (750 ml) is then added, and after decantation the clear aqueous layer is discarded. The organic phase washed with brine (500 ml), dried over sodium sulfate, filtered and concentrated to half of the original volume by evaporation in vacuo. The resulting residue is filtered on a pad of silica gel, eluting first with dichloromethane, then with ethyl acetate, and finally with a mixture of ethyl acetate and methanol (1:1). Concentration in vacuo gives a white foam which is triturated with diisopropyl ether to give: (20R,S)-16α,17α-butylidenedioxy-6α, 9α-difluoro-11β-hydroxy-3-oxoandrost-4-ene-17β-carboxylic acid as an off-white solid (12.7 g,27.7 mmol), m.p.210° C. (dec.); [NMR(DMSO,d6): 0.87(t,3H), 0.93(s, 2.7H),0.96(s,0.3H), 1.25–1.60(m,6H), 1.49(s,3H), 1.75(d, 2H), 1.91–2.0(m,2H), 2.0–2.1 (m, 1H), 2.16(c, 1H), 2.22–2.37(m,2H), 2.37–2.55(m,2H), 4.15(c, 1H), 4.68(t, 0.9H), 4.89(c,0.9H), 5.10(d,0.1H), 5.15(c,1H), 5.21 (t,0.1H), 5.50(c, 1H), 5.70(s,0.1H), 5.81 (s,0.9H)];

6.2) (20R,S)-16α,17α-Butylidenedioxy-6α,9α-difluoro-11β-hydroxy-3-oxoandrosta-4-ene-17β-carboxylic diethyl phosphoric anhydride By proceeding as described in the Reference Examples, (20R,S)-16α,17α-butylidenedioxy-6α,9α-difluoro-11β- hydroxy-3-oxoandrosta-4-ene-17β-carboxylic acid (12.6 g,27.7 mmol) gives (20R,S)-16α,17α-butylidenedioxy-6α, 9α-difluoro-11β-hydroxy-3-oxoandrosta-4-ene-17β-carboxylic diethyl phosphoric anhydride (17.2 g crude) which is used without further purification in the next step.

6.3) 2-Thioxo-1,2-dihydropyrid-1-yl (20R,S)-16α,17α-butylidenedioxy-6α,9α-difluoro-11β-hydroxy-3-oxoandrosta-4-ene-17β-carboxylate By proceeding as described in the Reference Examples, (20R,S)-16α,17α-butylidenedioxy-6α,9α-difluoro-11β-hydroxy-3-oxoandrosta-4-ene-17β-carboxylic diethyl phosphoric anhydride (17.2 g) gives after work up 2-thioxo-1, 2-dihydropyrid-1-yl (20R,S)-16α,17α-butylidenedioxy-6α, 9α-difluoro-11β-hydroxy-3-oxoandrosta-4-ene-17β-carboxylate (16.6 g) which is used as such in the next step.

6.4) (20R,S)-6α,9α-Difluoro-11β-hydroxy-16α,-17α-butylidenedioxy-17β-methylthioandrost-4-en-3-one By proceeding as described in Example 1, 2-thioxo-1,2-dihydropyrid-1-yl (20R,S)-3-oxo-6α,9α-difluoro-11β-hydroxy-16α,17α-butylidenedioxyandrost-4-ene-17β-carboxylate (16.6 g), as starting material affords after work up an off-white powder (12 g) which is purified by low pressure liquid chromatography on silica gel, eluting with a mixture of diethyl ether and petroleum spirit (75:25). The white solid obtained (6 g) is recrystallised from acetonitrile to give (20R,S)-6α,9α-difluoro-11β-hydroxy-16α,17α-butylidenedioxy-17β-methylthioandrost-4-en-3-one (4 g) as a mixture of epimers (20R,S) in proportions 90:10, which is resolved by preparative HPLC using a Dynamax RP-18 column and methanol/water as mobile phase. The (20R)-epimer is obtained as a white solid (3.4 g,7.45 mmol), m.p.180° C.; [NMR(DMSO,d6): 0.90(t,3H), 1.15(s,3H), 1.36–1.54(m,7H), 1.49(s,3H), 1.72(d,1H), 1.93–2.1 0(m, 3H), 2.09(s,3H), 2.16(c,1H), 2.23–2.38(m,2H), 2.28–2.54 (m,2H), 4.13(c,1H), 4.17(d,1H), 5.12(c,1H), 5.15(t,1H), 5.50(c,1H), 5.81 (s,1H), Found: C,63.3;H,7.60%. Calculated for $C_{24}H_{34}F_2O_4S$: C,63.1:H,7.51%].

6.5) (20R,S)-9α-Fluoro-11β-hydroxy-16α,17α-butylidenedioxy-17β-methylthioandrost-4-en-3-one In an analogous manner 2-thioxo-1,2-dihydropyrid-1-yl (20R,S)-3-oxo-9α-fluoro-11β-hydroxy-16α,17α-butylidenedioxyandrost-4-ene-17β-carboxylate (2.41 g) gives, after purification by low pressure liquid chromatography on silica gel eluting with a mixture of diethyl ether and petroleum spirit (9:1) and recrystallisation from cyclohexane, (20R,S)-9α-fluoro-11β-hydroxy-16α,17α-butylidenedioxy-17β-methylthioandrost-4-en-3-one as a white solid (0.58 g,1.32 mmol) in a stereoisomeric ratio of 90:10, m.p.161°–163° C.; [NMR(DMSO,d6): 0.89(t,3H), 1.05(s,0.3H), 1.14(s,2.7H), 1.25–1.75(m,9H), 1.48(s,0.3H), 1.49(s,2.7H), 1.92–2.10(m,3H), 2.03(s,0.3H), 2.09(s,2.7H), 2.18–2.60(m,6H), 4.10(c,1H), 4.13(d,0.9H), 4.75(d,0.1H), 5.03(c,0.9H), 5.0(c,0.1H), 5.10(t,0.1H), 5.14(t,0.9H), 5.68 (s,1H); Found: C,65.4;H,8.10%. Calculated for $C_{24}H_{35}FO_4S$: C,65.72:H,8.04%].

6.6) (20R)-6α,9α-Difluoro-11β-hydroxy-16α,17α-butylidenedioxy-17β-fluoromethylthioandrost-4-en-3-one By proceeding in a similar manner,(20R)-6α,9α-difluoro-11β-hydroxy-16α,17α-butylidenedioxy-17β-methylthioandrost-4-en-3-one (1.04 g,2.28 mmol) gives after work up a white foam (1.05 g) which is purified by low pressure liquid chromatography on silica gel eluting with a mixture of dichloromethane and methanol (99:1), to give (20R)-6α,9α-difluoro-11β-hydroxy-16α,17α-butylidenedioxy-17β-fluoromethylthioandrost-4-en-3-one (0.11 g,0.23 mmol), m.p. 185°–188° C.; [NMR(DMSO,d6): 0.89(t,3H), 1.05(s,3H), 1.33–1.66(m,7H), 1.49(s,3H), 1.73 (d,1H), 1.85–2.0(m,2H), 2.08(dt,1H), 2.19(c,1H), 2.03–2.36 (m,2H), 2.40–2.52(m,2H), 4.15(c,1H), 4.39(d,1H), 5.10(t, 1H), 5.25(d,1H), 5.50(c,1H), 5.60(dd,1H), 5.73(dd,1H), 5.81(s,1H); Calculated for $C_{24}H_{33}F_3O_4S$: C,60.75:H,7.01 %].

Found: C,60.9;H,7.10%.

EXAMPLE 7

7.1) (20R)-16α,17α-Butylidenedioxy-6α,9α-difluoro-11β-hydroxy-17β-(methylsulphinyl)androsta-1,4-dien-3-one (20R)-16α,17α-Butylidenedioxy-6α,9α-difluoro-11β-hydroxy-17β-methylthioandrosta-1,4-diene-3-one (3 g, 6.6 mmol) in solution in acetone (90 ml) is treated dropwise with a solution of potassium peroxymonosulfate (2.1 g, 3.36 mmol) in water (18 ml). After stirring for 40 minutes the reaction mixture is filtered and the filtrate concentrated in vacuo to give a pale yellow gum. This gum is taken up in chloroform (200 ml), washed with water (two times 200 ml) and brine (200 ml), dried over magnesium sulfate and concentrated in vacuo to give a pale yellow foam. This foam is purified by low pressure liquid chromatography on silica gel to give (20R)-16α,17α-butylidenedioxy-6α,9α-difluoro-11β-hydroxy-17β-(methylsulphinyl)androsta-1,4-dien-3-one-as a white solid (0.65 g,1.4 mmol), m.p.179°–180° C.; [NMR(DMSO,d6): 0.87(t,3H), 1.03(s, 3H), 1.30–1.48(m,3H), 1.49(s,3H), 1.49–1.82(m,5H), 1.85–2.0(m,2H), 2.29(c,1H), 2.54–2.70(m,1H), 2.63(s,3H), 4.15(c,1H), 5.12(d,1H), 5.41(c,1H), 5.47(c,1H), 5.65(c,1H), 6.10(s,1H), 6.29(dd,1H), 7.25(dd,1H); Calculated for $C_{24}H_{32}F_2O_5S$: C,61.3:H,6.85%].

Found: C,61.2;H.6.91%.

7.2) (20R)-9α-Fluoro-11β-hydroxy-16α,17α-butylidenedioxy-17β-methylsulphinylandrosta-1,4-dien-3-one (20R)-9α-Fluoro-11β-hydroxy-16α,17α-butylidenedioxy-17β-methylthioandrosta-1,4-dien-3-one (1 g,2.3 mmol) as starting material gives in an analogous manner to that described above (20R)-9α-fluoro-11β-hydroxy-16α,17α-butylidenedioxy-17β-methylsulphinylandrosta-1,4-dien-3-one as a white solid (0.25 g,0.55 mmol), m.p.175° C.; [NMR(DMSO,d6): 0.87 (t,3H), 1.04(s,3H), 1.28–1.43(m,3H), 1.43–1.99(m,8H), 1.49(s,3H), 2.35(dd,1H), 2.35–2.70(m,2H), 2.65(s,3H), 4.15 (c,1H), 5.10(d,1H), 5.32(c,1H),,5.48(t,1H),6.03(s,1H),,6.23 (dd,1H),,7.27(d,1H); Calculated for $C_{24}H_{33}FO_5S$: C,63.7:H, 7.35%].

Found: C,63.4;H,7.40%.

EXAMPLE 8

8.1) (20R)-6α,9α-Difluoro-11β-hydroxy-16α,17α-butylidenedioxy-17β-methylsulphonylandrosta-1,4-dien-3-one (20R)-6α,9α-Difluoro-11β-hydroxy-16α,17α-butylidenedioxy-17β-methylsulphinylandrosta-1,4-dien-3-one (0.3 g,0.64 mmol) in solution in chloroform (20 ml) is treated at 25° C. with 3-chloroperoxybenzoic acid (0.24 g, 1.4 mmol) and the mixture is stirred for 1 hour. The reaction mixture is treated with an aqueous solution of sodium sulfite then washed successively with water (two times 25 ml), an aqueous solution of sodium carbonate (2M, two times 25 ml), water (25 ml), and brine (25 ml), then dried over magnesium sulfate and concentrated in vacuo to give a colorless foam which is triturated in hot diisopropyl ether to give (20R)-6α,9α-difluoro-11β-hydroxy-16α,17α-butylidenedioxy-17β-methylsulphonylandrosta-1,4-dien-3-one as a white solid (0.2 g,0.41 mmol),m.p.149°–150° C.; [NMR(DMSO,d6): 0.87(t,3H), 1.29(s,3H), 1.29–1.48 (m,3H), 1.50(s,3H), 1.53–1.60(m,2H), 1.66–1.77 (m,2H), 1.87(d,1H), 190-2.05(m,2H), 2.29(c,1H), 2.60-2.76(m,1H), 3.0(s,3H), 4.20(c,1H), 4.49(d,1H), 5.46(t,1H), 5.50(c,1H), 5.65(c,1H), 6.12(s,1H), 6.30(dd,1H), 7.27(dd,1H); Calculated for $C_{24}H_{32}F_2O_6S$: C,59.2;H,6.63%|.
Found: C,58.8;H,6.61%.

EXAMPLE 9

9.1) 9α-Fluoro-11β-hydroxy-16α,17α-isopropylidenedioxy-17β-methylsulphonylandrosta-1,4-dien-3-one 9α-Fluoro-11β-hydroxy-16α,17α-isopropylidenedioxy-17β-methylthio-androsta-1,4-dien-3-one (1.4 g,3.3 mmol) in solution in chloroform (150 ml) is treated with 3-chloroperoxybenzoic acid (2.2 g,6.8 mmol) at 25° C. When the reaction is completed (t.l.c.), the reaction mixture is worked up as described above and the residue obtained is purified by low pressure liquid chromatography on silica gel, eluting with a mixture of chloroform and methanol (95:5). Recrystallization from a mixture of acetone and hexane gives 9α-fluoro-11β-hydroxy-16α,17α-isopropylidenedioxy-17β-methylsulphonylandrosta-1,4-dien-3-one as a white powder (0.24 g,0.53 mmol), m.p. 180° C. (dec.); [NMR(DMSO,d6): 1.29(s,3H), 1.29-1.42(m,1H), 1.44(s,3H), 1.50(s,3H), 1.52(s,3H), 1.59(dd,1H), 1.73-1.88 (m,3H), 1.99(dt,1H), 2.1 0(dt,1H), 2.35(dd,1H), 2.49-2.70 (m,2H), 2.96(s,3H), 4.18(c,1H), 5.15(d,1H), 5.40(c,1H), 6.03(s,1H), 6.24(dd,1H), 7.28(d,1H); Calculated for $C_{23}H_{31}FO_6S$: C,60.7;H,6.90%|.
Found: C,61.0;H,7.00%.

EXAMPLE 10

10.1) (20S)-16α,17α-Butylidenedioxy-6α,9α-difluoro-11β-hydroxy-17β-(methylthio)androst-4-ene-3-one A stirred mixture of (20S)-16α,17α-butylidenedioxy-6α,9α-difluoro-11β-hydroxy-17β-(methylthio)androsta-1,4-diene-3-one( (0.16 g) in ethanol (2 ml) is purged with nitrogen then treated with a catalytic amount of rhodium tris(triphenyl phosphine ) chloride. The reaction mixture is stirred under a positive pressure of hydrogen until one equivalent had been taken up. The reaction mixture is washed with water (50 ml) and concentrated in vacuo. The residue is purified by low pressure liquid chromatography on silica gel eluting with ethyl acetate/ cyclohexane 1/1 to give (20S)-16α,17α-butylidenedioxy-6α,9α-difluoro-11β-hydroxy-17β-(methylthio)androst-4-ene-3-one (0.15 g) as an off white powder.

Calculated for $C_{24}H_{34}F_2O_4S$: C, 63.1; H, 7.51. Found: C, 63.3;H,7.6%

EXAMPLE 11

11.1) (20R)-16α,17α-butylidenedioxy-6α,9α-difluoro-11β-hydroxy-17β-(methylthio)androstan-3-one By proceeding as described in Example 1, 2-thioxo-1,2-dihydropyrid-1-yl (20R)-16α,17α-butylidenedioxy-6α,9α-difluoro-11β-hydroxy-3-oxoandrostane-17β-carboxylate as starting material affords after work up and low pressure liquid chromatography on silica gel eluting with ethyl acetate/ cyclohexane 1/1 gives (20R)-16α,17β-butylidenedioxy-6α,9α-difluoro-11β-hydroxy-17β-(methylthio)androstan-3-one (as an off white solid).

Calculated for $C_{24}H_{36}F_2O_4S$: C, 62.9; H, 7.9; Found: C,62.6; H, 7.9

EXAMPLE 12

12.1) (20R)-16α,17α-Butylidenedioxy-9α-fluoro-11β-hydroxy-17β-(methylthio)androst-4-en-3,6-dione A solution of (20R)-16α,17α-butylidenedioxy-9α-fluoro-11β-hydroxy-17β-(methylthio)androsta-1,4-diene-3,6-dione (0.15 g) in toluene (2 ml) and ethanol (2 ml) is purged with nitrogen, treated with rhodium tris(triphenyl phosphine ) chloride (0.015 g) and hydrogenated at 0.3 bar over night, heated at 50° C. for 6 hours and left to stand for 3 days. The reaction mixture is concentrated in vacuo and chromatographed on silica gel eluting with ethyl acetate/cyclohexane 1/2 to give (20R)-16α,17α-butylidenedioxy-9α-fluoro-11β-hydroxy-17β-(methylthio)-androst-4-en-3,6-dione (0.08 g) as an off white powder.

Calculated for $C_{24}H_{33}FO_5S$: C, 63.7; H, 7.35. Found: C, 64.0; H, 7.5

Reference Example 1

R. E. 1.1) (20R,S)-16α,17α-Butylidenedioxy-9α-fluoro-11β-hydroxy-3-oxoandrosta-1,4-diene-17β-carboxylic acid To a well stirred suspension of 9α-fluoro-11β,16α,17α-trihydroxy-3-oxoandrosta-1,4-diene-17β-carboxylic acid (7.9 g, 20 mmol) in tetrahydrofuran (65 ml) at 25° C. is added butyraldehyde (9.2 ml, 100 mmol) and perchloric acid (0.2 g, 1.97 mmol). When the reaction mixture is homogeneous (1–5 hrs), the perchloric acid is neutralized by addition of triethylamine (0.2 g, 1.97 mmol). Evaporation of the solvent in vacuo gives a solid which is dissolved in sodium hydroxide (2N) and the resulting aqueous solution is washed several times with diethyl ether. Neutralization of this aqueous solution with hydrochloric acid (10N) gives a white precipitate which is filtered off, washed with water and dried under vacuum at 80° C. overnight: (20R,S)-16α,17α-butylidenedioxy-9α-fluoro-11β-hydroxy-3-oxoandrosta-1,4-diene-17β-carboxylic acid (8.5 g, 18.3 mmol), m.p. 205° C. (dec.); [N.M.R. (DMSO, d6): 0.85 (m, 3H), 0.96 (s, 3H), 1.22–1.46 (c, 4H), 1.50 (s, 3H), 1.49–1.61 (m, 3H), 1.70–1.97 (m, 4H), 2.33 (dd,1H), 2.34–2.50 (m, 1H), 2.62 (dt, 1H), 4.15 (c, 1H), 4.67 (t, 0.9H), 4.85 (d, 0.9H), 5.08 (d, 0.1H), 5.16 (t, 0.1H), 5.89 (m, 1H), 6.01 (s, 1H), 6.23 (dd, 1H), 7.29 (d, 1H)]. This compound is used in the next step without further purification.

Reference Example 2

R. E. 2.1) (20R,S)-16α,17α-Butylidenedioxy-6α,9α-difluoro-11β-hydroxy-3-oxoandrosta-1,4-diene-17β-carboxylic acid To a stirred suspension of 6α,9α-difluoro-11β,16α,17α-trihydroxy-3-oxoandrosta-1,4-diene-17β-carboxylic acid (50 g, 126 mmol) in tetrahydrofuran (2 l) at 25° C. under a nitrogen atmosphere is added butyraldehyde (59.2 g, 820 mmol) and perchloric acid (1.2 g, 11.8 mmol). The reaction mixture is stirred for 16 hours then treated dropwise with triethylamine (1.2 g, 11.8 mmol). Evaporation of the solvent in vacuo gives a yellow oil which is partitioned between ethyl acetate (1 l) and sodium carbonate (2N). The aqueous phase is decanted, washed with more ethyl acetate (400 ml), acidified to pH 2 with hydrochloric acid (10N) before being extracted with diethyl ether (1 l). The combined diethyl ether extracts were washed with water, brine then dried over magnesium sulfate. Filtration of the dessicant and evaporation of the solvent in vacuo gives a white solid which is triturated with cyclohexane before being dried under vacuum at 80° C. overnight: (20R,S)-16α,17α-butylidenedioxy-6α,9α-difluoro-11β-hydroxy-3-oxoandrosta-1,4-diene-17β-carboxylic acid (54.8 g, 121 mmol); [N.M.R. (DMSO, d6): 0.85 (m, 3H), 0.96 (s, 3H), 1.22–1.46 (c, 4H), 1.50 (s, 3H), 1.49–1.62 (m, 3H), 1.79 (c,1H), 1.90–2.06 (m, 3H), 2.26 (c,1H), 2.45–2.67 (m, 1H), 4.17 (c, 1H), 4.68 (t, 0.8H), 4.88 (d, 0.8H), 5.10 (d, 0.2H), 5.19 (t, 0.2H), 5.45 (d, 1H), 5.63 (c, 1H), 6.10 (s, 1H), 6.29 (dd, 1H), 7.35 (d, 1H)]. This compound is used in the next step without further purification.

R. E. 2.2) (20R,S)-16α,17α-[(E)-2-Butenylidenedioxy]-9α-fluoro-11β-hydroxy-3-oxoandrosta-1,4-diene-17β-carboxylic acid In an analogous manner using 9a-fluoro-11β,16α,17α-trihydroxy-3-oxoandrosta-1,4-diene-17β-carboxylic acid (8.9 g, 23.4 mmol) and crotonaldehyde (7.4 g, 105.3 mmol) as starting materials gives after work up (20R,S)-16α,17α-[(E)-2-butenylidenedioxy]-9α-fluoro-11β-hydroxy-3-oxoandrosta-1,4-diene-17β-carboxylic acid (9.1 g, 21 mmol); [N.M.R. (DMSO, d6): 0.96 (s, 3H), 1.30–1.43 (m, 1H), 1.50 (s, 3H), 1.47–1.60 (m, 2H), 1.64 (dd, 0.6H), 1.68 (dd, 2.4H), 1.68–2.0 (m, 5H), 2.34 (dd, 1H), 2.35–2.52 (m, 1H), (dt, 1H),4.15 (c, 1H), 4.85 (d, 0.8H), 4.97 (d, 0.8H), 5.07 (d, 0.2H), 5.28 (ddd, 0.2H), 5.33–5.40 (m, 1.8H), 5.46 (d, 0.2 H), 2.64 5.85 (m, 0.2H), 5.92 (m, 0.8H), 6.03 (s,1H), 6.23 (dd, 1H), 7.29 (d, 1H)]. This compound is used as such in the next step.

R. E. 2.3) (20R, S)-16α,17α-Butylidenedioxy-9α-fluoro-11β-hydroxy-3,6-dioxoandrosta-1,4-diene-17β-carboxylic acid By proceding in an analogous manner but using 9α-fluoro-11β,16α,17α-trihydroxy-3,6-dioxoandrosta-1,4-diene-17β-carboxylic acid (2.1 g) gives after work up (20R, S)-16α,17α-butylidenedioxy-9α-fluoro-11β-hydroxy-3,6-dioxoandrosta-1,4-diene-17β-carboxylic acid((1.6 g); [N.M.R. (DMSO, d6): 0.8–0.9 (m, 3H), 0.97 (s,3H), 1.2–1.45 (m, 3H), 1.47 (s, 3H), 1.48–1.65 (m, 3H), 1.8–1.9 (m, 1H), 2–2.2 (m, 2H), 2.25–2.35 (m, 1H), 2.6–2.95 (m, 2H), 4.2–4.23 (c,1H), 4.68 (t, 0.8H), 4.88 (d, 0.8H), 5.1 (d, 0.2H), 5.23 (t, 0.2H), 5.52 (c, 0.2H), 5.62 (c, 0.8H), 6.29 (d, 1H), 6.4 (dd, 1H), 7.41 (2d, 1H)].

R. E. 2.4) (20R,S)-16α,17α-Butylidenedioxy-9α-fluoro-11β-hydroxy-3-oxoandrost-4-ene-17β-carboxylic acid 9α-Fluoro-11β-16α,17α-trihydroxy-3-oxoandrost-4-ene-17β-carboxylic acid (2.4 g) gives in a manner analogous to that described above (20R,S)-16α,17α-butylidenedioxy-9α-fluoro-11β-hydroxy-3-oxoandrost-4-ene-17β-carboxylic acid (2.15 g).

Reference Example 3

R. E. 3.1) 9α-Fluoro-11β-hydroxy-16α,17α-isopropylidenedioxy-3-oxoandrosta-1,4-diene-17β-carboxylic acid 9α-Fluoro-11β,16α,17α-trihydroxy-3-oxoandrosta-1,4-diene-17β-carboxylic acid (7.9 g, 20 mmol) is suspended in acetone (100 ml) then perchloric acid (0.2 g, 1.97 mmol) is added at 25° C. 9α-fluoro-11β-hydroxy-16α,17α-isopropylidenedioxy-3-oxoandrosta-1,4-diene-17β-carboxylic acid is isolated after work up as a white solid (7 g, 16.7 mmol) in a manner analogous to that described above, m.p. 316° C. (dec.); [N.M.R. (DMSO, d6): 0.94 (s, 3H), 1.15 (s, 3H), 1.20 (s, 3H), 1.26–1.40 (m, 1H), 1.49 (s, 3H), 1.47–1.51 (m, 1H), 1.53–1.62 (dt, 1H), 1.68 (d, 1H), 1.69–1.95 (m, 3H), 2.33 (dd, 1H), 2.35–2.52 (m, 1H), 2.64 (dt, 1H), 4.15 (c, 1H), 4.95 (d, 1H), 6.34 (m, 1H), 6.02 (s, 1H), 6.21 (dd, 1H), 7.27 (d, 1H)] which is used as such in the next step.

R. E. 3.2) 6α,9α-Difluoro-11β-hydroxy-16α,17α-isopropyli-denedioxy-3-oxoandrosta-1,4-diene-17β-carboxylic acid In an analogous manner 6α,9α-difluoro-11β,16α,17α-trihydroxy-3-oxoandrosta-1,4-diene-17β-carboxylic acid (45.0 g, 112.9 mmol) gives after work up 6α,9α-difluoro-11β-hydroxy-16α,17α-isopropylidenedioxy-3-oxoandrosta-1,4-diene-17β-carboxylic acid (40.9 g, 93.3 mmol), m.p. 285°–7° C. (dec.); [N.M.R. (DMSO, d6): 0.93 (s, 3H), 1.15 (s, 3H), 1.31 (s, 3H), 1.40–1.67 (m, 4H), 1.50 (s, 3H), 1.69 (d,1H), 1.80–2.02 (m, 2H), 2.26 (c, 1H), 2.48–2.65 (m, 1H), 4.17 (c, 1H), 4.97 (d, 1H), 5.43 (c, 1H), 5.64 (m, 1H), 6.10 (s, 1H), 6.28 (dd, 1H), 7.27 (dd, 1H)] which is used as such in the next step.

Reference Example 4

R. E. 4.1) 9α-Fluoro-11β-hydroxy-16α,17α-isopropylidene-dioxy-3-oxoandrosta-1,4-diene-17β-carboxylic diethyl phosphoric anhydride To a stirred solution of 9α-fluoro-11β-hydroxy-16α,17α-isopropyl-idenedioxy-3-oxoandrosta-1,4-diene-17β-carboxylic acid (1.05 g, 2.5 mmol) in tetrahydrofuran (35 ml) containing activated molecular sieve (type 4 A, 1 g) at 25° C. under an atmosphere of nitrogen is added triethylamine (0.7 ml, 5 mmol). After stirring for 0.5 hour the reaction mixture is treated with diethyl chlorophosphate (0.54 ml, 3.75 mmol) over a period of 45 minutes and stirred for a further 90 minutes. The resulting mixture is filtered through a pad of celite and the tetrahydrofuran evaporated in vacuo, the crude oil obtained is taken up in ethyl acetate (50 ml), washed with hydrochloric acid (1N, 25 ml) then with water (two times 25 ml) and brine (two times 25 ml). The ethyl acetate phase is dried over sodium sulphate, the dessicant is then filtered off and concentration in vacuo affords the 9α-fluoro-11β-hydroxy-16α,17α-isopropylidenedioxy- 3-oxoandrosta-1,4-diene-17β-carboxylic diethyl phosphoric anhydride as a crude yellow oil (1.5 g) which is used without further purification in the next step.

R. E. 4.2) 6α,9α-Difluoro-11β-hydroxy-16α,17α-isopropylidenedioxy-3-oxoandrosta-1,4-diene-17β-carboxylic diethyl phosphoric anhydride I 6α,9α-Difluoro-11β-hydroxy-16α,17α-isopropylidenedioxy-3-oxoandrosta-1,4-diene-17β-carboxylic acid (7.04 g, 16 mmol) gives in an manner analogous to that described above 6α,9α-difluoro-11β-hydroxy-16α,17α-isopropyl-idenedioxy-3-oxoandrosta-1,4-diene-17β-carboxylic diethyl phosphoric anhydride as a crude white foam (9.8 g) which is used as such in the next step.

R. E. 4.3) (20R,S)-16α,17α-Butylidenedioxy-6α,9α-difluoro-11β-hydroxy-3-oxoandrosta-1,4-diene-17β-carboxylic diethyl phosphoric anhydride (20R,S)-16α,17α-Butylidenedioxy-6α,9α-difluoro-11β-hydroxy-3-oxoandrosta-1,4-diene-17β-carboxylic acid (14.5 g, 32 mmol) gives in an manner analogous to that described above (20R,S)-16α,17α-butylidenedioxy-6α,9α-difluoro-11β-hydroxy-3-oxoandrosta-1,4-diene-17β-carboxylic diethyl phosphoric anhydride (19.5 g crude) which is used as such in the next step.

R. E. 4.4) (20R,S)-16α,17α-[(E)-2-Butenylidenedioxy]-9α-fluoro-11β-hydroxy-3-oxoandrosta-1,4-diene-17β-carboxylic diethyl phosphoric anhydride (20R,S)-16α,17α-[(E)-2-Butenylidenedioxy]-9α-fluoro-11β-hydroxy-3-oxoandrosta-1,4-diene-17β-carboxylic acid (10.0 g, 23.1 mmol) gives in an manner analogous to that described above (20R,S)-16α,17α-[(E)-2-butenylidenedioxy]-9α-fluoro-11β-hydroxy-3-oxoandrosta-1,4-diene-17β-carboxylic diethyl phosphoric anhydride (13 g crude) which is used without further purification in the next step.

R. E. 4.5) (20R,S)-16α,17α-Butylidenedioxy-9α-fluoro-11β-hydroxy-3-oxoandrosta-1,4-diene-17β-carboxylic diethyl-phosphoric anhydride In an analogous manner using (20R,S)-16α,17α-butylidenedioxy-9α-fluoro-11β-hydroxy-3-oxoandrosta-1,4-diene-17β-carboxylic acid (6.4 g, 15.2 mmol) as starting material gives the crude (20R,S)-16α,17α-butylidenedioxy-9α-fluoro-11β-hydroxy-3-oxoandrosta-1,4-diene-17β-carboxylic diethyl phosphoric anhydride as a crude yellow oil (7.5 g) which is used as such in the next step.

R. E. 4.6) (20R,S)-16α,17α-Butylidenedioxy-9α-fluoro-11β-hydroxy-3,6-dioxoandrosta-1,4-diene-17β-carboxylic diethyl phosphoric anhydride In an analogous manner using (20R,S)-16α,17α-butylidenedioxy-9α-fluoro-11β-hydroxy-3,6-dioxoandrosta-1,4-diene-17β-carboxylic acid (1.46 g) gives in a manner analogous to that described above (20R,S)-16α,17α-butylidenedioxy-9α-fluoro-11β-hydroxy-3,6-dioxoandrosta-1,4-diene-17β-carboxylic diethyl phosphoric anhydride (2.06 g crude ).

R. E. 4.7) (20R)-6α,9α-Difluoro-11β-hydroxy-16α,17α-butylidenedioxy-3-oxoandrostane-17β-carboxylic diethyl phosphoric anhydride (20R)-16α,17α-Butylidenedioxy-6α,9α-difluoro-11β-hydroxy-3-oxoandrostane-17β-carboxylic acid( (2 g) gives in a manner analogous to that described above (20R)-6α,9α-difluoro-11β-hydroxy-16α,17α-butylidenedioxy-3-oxoandrostane-17β-carboxylic diethyl phosphoric anhydride.

R. E. 4.8) (20R,S)-16α,17α-Butylidenedioxy-9α-fluoro-11β-hydroxy-3-oxoandrost-4-ene-17β-carboxylic diethyl phosphoric anhydride (20R, S)-16α,17α-Butylidenedioxy-9α-fluoro-11β-hydroxy-3-oxoandrost-4-ene-17β-carboxylic acid (2.1 g) gives in a manner analogous to that described above (20R, S)-16α,17α-butylidenedioxy-9α-fluoro-11β-hydroxy-3-oxoandrost-4-ene-17β-carboxylic diethyl phosphoric anhydride (2.8 g).

Reference Example 5

R. E. 5.1) 2-Thioxo-1,2-dihydropyrid-1-yl 9α-fluoro-11β-hydroxy-16α,17α-isopropylidenedioxy-3-oxoandrosta-1,4-diene-17β-carboxylate In a reaction vessel protected from light, a stirred solution of 9α-fluoro-11β-hydroxy-16α,17α-isopropylidenedioxy-3-oxoandrosta-1,4-diene-17β-carboxylic diethyl phosphoric anhydride (3.4 g) in dimethyl-formamide (30 ml) containing activated molecular sieve (type 4 A, 5 g) and maintained at 20° C. under a nitrogen atmosphere is treated with the sodium salt of 2-mercaptopyridine N-oxide (1. 13 g, 7.6 mmol). After the reaction is completed (t.l.c.), the reaction mixture is filtered and the filtrate poured into ice cold water (150 ml). The yellow precipitate formed is collected by filtration, washed with cold water then taken up in dichloromethane (100 ml), washed with cold water, brine then dried over sodium sulphate. The dessicant is filtered off, the clear yellow solution concentrated in vacuo (20° C.; 13 mmHg) to give a bright yellow precipitate of 2-thioxo-1,2-dihydropyrid-1-yl 9α-fluoro-11β-hydroxy-16α,17α-isopropylidene-dioxy-3-oxoandrosta-1,4-diene-17β-carboxylate (2.5 g) which is used as such in the next step. All the above procedures are carried out with exclusion of light as far as is practicable.

R. E. 5.2) 2-Thioxo-1,2-dihydropyrid-1-yl 6α,9α-difluoro-11β-hydroxy-16α,17α-isopropylidenedioxy-3-oxoandrosta-1,4-diene-17β-carboxylate 6α,9α-Difluoro-11β-hydroxy-16α,17α-isopropylidenedioxy-3-oxoandrosta-1,4-diene-17β-carboxylic diethyl phosphoric anhydride (9.7 g) gives in a manner analogous to that described above 2-thioxo-1,2-dihydropyrid-1-yl 6α,9α-difluoro-11β-hydroxy-16α,17α-isopropylidenedioxy-3-oxoandrosta-1,4-diene-17β-carboxylate (8.41 g) which is used as such in the next step.

R. E. 5.3) 2-Thioxo-1,2-dihydropyrid-1-yl (20R,S)-16α,17-αbutylidenedioxy-6α,9α-difluoro-11β-hydroxy-3-oxoandrosta-1,4-diene-17β-carboxylate (20R,S)-16α,17α-Butylidenedioxy-6α,9α-difluoro-11β-hydroxy-3-oxoandrosta-1,4-diene-17β-carboxylic diethyl phosphoric anhydride(19.5 g) gives after work up 2-thioxo-1,2-dihydropyrid-1-yl (20R,S)-16α,17α-butylidenedioxy-6α,9α-difluoro-11β-hydroxy-3-oxoandrosta-1,4-diene-17β-carboxylate (19.5 g) which is used in the next step without further purification.

R. E. 5.4) 2-Thioxo-1,2-dihydropyrid-1-yl (20R,S)-16α,17α-|(E)-2-butenylidenedioxy|-9α-fluoro-11β-hydroxy-3-oxoandrosta-1,4-diene-17β-carboxylate (20R,S)-16α,17α-|(E)-2-Butenylidenedioxy|-9α-fluoro-11β-hydroxy-3-oxoandrosta-1,4-diene-17β-carboxylic diethyl phosphoric anhydride. (2 g) gives after work up 2-thioxo-1,2-dihydropyrid-1-yl (20R,S)-16α,17α-|(E)-2-butenylidenedioxy|-9α-fluoro-11β-hydroxy-3-oxoandrosta-1,4-diene-17β-carboxylate (1.90 g) which is used as such in the next step.

R. E. 5.5) 2-Thioxo-1,2-dihydropyrid-1-yl (20R,S)-16α,17α-butylidenedioxy-9α-fluoro-11β-hydroxy-3-oxoandrosta-1,4-diene-17β-carboxylate An analogous procedure using (20R,S)-16α,17α-butylidenedioxy-9α-fluoro-11β-hydroxy-3-oxoandrosta-1,4-diene-17β-carboxylic diethyl phosphoric anhydride (4.2 g) as starting material affords 2-thioxo-1,2-dihydropyrid-1-yl (20R,S)-16α,17α-butylidenedioxy-9α-fluoro-11β-hydroxy-3-oxoandrosta-1,4-diene-17β-carboxylate (3 g) which is used in the next step without further purification.

R. E. 5.6) 2-Thioxo-1,2-dihydropyrid-1-yl (20R,S)-16α,17α-butylidenedioxy-9α-fluoro-11β-hydroxy-3,6-dioxoandrosta-1,4-diene-17β-carboxylate An analogous procedure using (20R,S)-16α,17α-butylidenedioxy-9α-fluoro-11β-hydroxy-3,6-dioxoandrosta-1,4-diene-17β-carboxylic diethyl phosphoric anhydride (2.0 g) gives after work up 2-thioxo-1,2-dihydropyrid-1-yl (20R,S)-16α,17α-butylidenedioxy-9α-fluoro-11β-hydroxy-3,6-dioxoandrosta-1,4-diene-17βp-carboxylate(1.83 g).

R. E. 5.7) 2-Thioxo-1,2-dihydropyrid-1-yl (20R)-16α,17α-butylidenedioxy-6α,9α-difluoro-11β-hydroxy-3-oxoandrostane-17β-carboxylate (20R)-16α,17α-Butylidenedioxy-6α,9α-difluoro-11β-hydroxy-3-oxoandrostane-17β-carboxylic diethyl phosphoric anhydride gives in a manner analogous to that described above 2-thioxo-1,2-dihydropyrid-1-yl (20R)-16α,17α-butylidenedioxy-6α,9α-difluoro-11β-hydroxy-3-oxoandrostane-17β-carboxylate.

R. E. 5.8 2-Thioxo-1,2-dihydropyrid-1-yl (20R,S)-16α,17α-butylidenedioxy-9α-fluoro-11β-hydroxy-3-oxoandrost-4-ene-17β-carboxylate (20R,S)-16α,17α-Butylidenedioxy-9α-fluoro-11β-hydroxy-3-oxoandrost-4-ene-17β-carboxylic diethyl phosphoric anhydride (2.8 g) gives in a manner analogous to that described above 2-thioxo-1,2-dihydropyrid-1-yl (20R,S)-16α,17α-butylidenedioxy-9α-fluoro-11β-hydroxy-3-oxoandrost-4-ene-17β-carboxylate (2.4 g).

Reference Example 6

R. E. 6) 9α-Fluoro-11β,16α,17α-trihydroxy-3,6-dioxoandrosta-1,4-diene-17β-carboxylic acid To a stirred mixture of 9α-fluoro-11β,16α,17α,21-tetrahydroxypregna-1,4-diene-3,6,20-trione (2.4 g) in dry dimethylformamide is added potassium superoxide (1.68 g) followed by 18-crown-6 (1.56 g). The reaction temperature rose to 48° C. and is cooled to 40° C. The reaction mixture is added to water (300 ml), acidified to pH9, washed with ethyl acetate (2 times ) and acidified to pH 2 (using concentrated hydrochloric acid) then extracted into ethyl acetate (3 times). The combined organic extracts were washed with brine then dried over magnesium sulfate. Filtration of the dessicant and concentration in vacuo gives 9α-fluoro-11β,16α,17α-trihydroxy-3,6-dioxoandrosta-1,4-diene-17β-carboxylic acid as an orange powder upon trituration with ethyl acetate (0.7 g). This is used as such in the next step.

Reference Example 7

R. E. 7.1) 9α-Fluoro-11β,16α,17α,21-tetrahydroxypregna-1,4-diene-3,6,20-trione

A stirred suspension of 21-acetyloxy-9α-fluoro-11β,16α,17α-trihydroxypregna-1,4-diene-3,6,20-trione (4.32 g) in degassed methanol (200 ml) and tetrahydrofuran (50 ml), under an inert atmosphere is treated with a solution of potassium carbonate (0.62 g) in water (10 ml) over one hour. The reaction mixture is acidified to pH 6 (dilute hydrochloric acid ), cooled to 0° C. and the preciptated solid filtered off and washed with cold methanol to give 9α-fluoro-11β,16α,17α,21-tetrahydroxypregna-1,4-diene-3,6,20-trione (2.78 g) as a buff powder m.p. 255°–6° C.

Reference Example 8

R. E. 8.1) 21-Acetyloxy-9α-fluoro-11β,16α,17α-trihydroxy-pregna-1,4-diene-3,6,20-trione A stirred solution of 21-Acetyloxy-9α-fluoro-11β-hydroxy-16α,17α-isopropylidenedioxy-pregna-1,4-diene-3,6,20-trione (6.7 g) in formic acid (200 ml), under an inert atmosphere is heated at 70°–75° C. for 6 hours and left to stand over night. The reaction mixture is concentrated in vacuo, taken up in toluene, and concentrated in vacuo again. The residue is suspended in methanol (40 ml) and treated slowly with concentrated ammonia solution until the pH of the reaction mixture is 9 or 10. The mixture is cooled to 0° C. and the precipitated solid filtered off, washed with cold methanol, and sucked dry to give 21-acetyloxy-9α-fluoro-11β,16α,17α-trihydroxypregna-1,4-diene-3,6,20-trione (4.32 g) as a pale yellow powder.

Reference Example 9

R. E. 9.1) (20R)-6α,9α-Difluoro-11β-hydroxy-16α,17α-butylidenedioxy-3-oxoandrostane-17β-carboxylic acid A stirred mixture of (20R)-16α,17α-butylidenedioxy-6α,9α-difluoro-11β-hydroxy-3-oxoandrost-4-ene-17β-carboxylic acid (5 g) in ethanol (100 ml) is purged with nitrogen, treated with 5% palladium on charcoal (5 g) and then hydrogenated at 0.3 bars for several hours. The reaction mixture is filtered through celite and the filtrate concentrated in vacuo to give (20R)-6α,9α-difluoro-11β-hydroxy-16α,17α-butylidenedioxy-3-oxoandrostane-17β-carboxylic acid (4.7 g) as a white foam.

Reference Example 10

R. E. 10.1) 9α-Fluoro-11β,16α,17α-trihydroxy-3-oxoandrost-4-ene-17β-carboxylic acid To a stirred mixture of 9α-fluoro-11β-16α,17α-21-tetrahydroxypregn-4-ene-3,20-dione (2 g) in dry dimethylformamide (30 ml) is added potassium superoxide (1.4 g) followed by 18-crown-6 (1.3 g) and cooling used to maintain the temperature at 25°–38° C. The reaction mixture is stirred for ½ an hour, treated with water (300 ml), acidified to pH 9, washed with ethyl acetate (2 times) then acidified to pH 2 ( using concentrated hydrochloric acid) and extracted with ethyl acetate (3 times ). The combined organic extracts were washed with brine and dried over magnesium sulfate. Filtration of the dessicant and concentration in vacuo gives 9α-fluoro-11β,16α,17α-trihydroxy-3-oxoandrost-4-ene-17β-carboxylic acid ( 0.9 g) as a white solid.

The present invention also includes within its scope pharmaceutical formulations which comprise an effective amount of at least one of the compounds of formula I in association with a pharmaceutically acceptable carrier or coating.

PHARMACOLOGICAL USES

An object of the invention is to provide a topical antiinflammatory, immunosuppressive and antiallergic steroid, or a pharmaceutical composition thereof, for the following:

topical treatment of skin conditions such as dermatitis, psoriasis, sunburn, eczema, neurodermatitis and ano-genital pruritis;

inhaled treatment of airways conditions such as allergy, asthma and rhinitis, chronic obstructive pulmonary disease, interstitial lung diseases and fibrosis;

local treatment of inflammatory bowel conditions such as ulcerative colitis and Crohn's disease; and local treatment of conjuctiva and conjunctivitis.

The topical treatment of such conditions by steroid compounds of this invention is associated with no side-effects or minimal side-effects associated with typical systemic steroid activity, such as suppression of hypothalamus-pituitary-adrenal function, mobilisation of glucose stores, collagen disorders, mineralocorticoid function, adrenal atrophy, osteoporosis and suppression of bone growth and atrophy of thymic tissue.

This may be achieved by a combination of direct delivery of the steroid to the application site, and by reduced systemic activity, caused by restricted absorption or by rapid in-vivo metabolism of the steroid. Thus, inactivation of the steroid can be by metabolism in the target organ or, after uptake into the general circulation, e.g. by metabolism or excretion. Such compounds are often referred to as "soft" steroids.

PHARMACOLOGICAL TEST SYSTEMS

Biological test results on compounds of this invention are exemplified as follows:

GLUCOCORTICOID AGONIST ACTIVITY
STEROID BINDING TO THE RAT THYMUS GLUCOCORTICOID RECEPTOR

Thymi of male adrenalectomised rats are removed and homogenised in 3-(N-morpholino)propanesulphonic acid dithiothreitol buffer, and centrifuged at 100,000 g. The supernatant cytosol is used as the source of receptor. Steroid (1–16 nM in doubling dilutions) and [$^3$H] dexamethasone (4 nM) are equilibrated with receptor for 24 hours at 4° C. Bound [$^3$H] dexamethasone is separated from free dexamethasone by a dextran coated charcoal technique and is quantified by liquid scintillation counting. The IC$_{50}$ (concentration reducing [$^3$H] dexamethasone binding by 50%) is calculated from the plot of the fraction bound against added steroid concentration.

The following results demonstrate the effectiveness of compounds of this invention when subjected to the above glucocoticoid receptor binding assay:

| | |
|---|---|
| 9α-fluoro-11β-hydroxy-16α,17α-isopropylidenedioxy-17β-methylthioandrosta-1,4-dien-3-one | 1.6 nM |
| (20R)-9α-fluoro-11β-hydroxy-16α,17α-butylidenedioxy-17β-methylthioandrosta-1,4-dien-3-one | 1.7 nM |
| (20R,S)-9α-fluoro-11β-hydroxy-16α,17α-butylidenedioxy-17β-(2-pyridylthio)androsta-1,4-dien-3-one | 11.3 nM |
| 9α-fluoro-11β-hydroxy-16α,17α-isopropylidenedioxy-17β-methylsulphonylandrosta-1,4-dien-3-one | 3.8 nM |
| (20R)-9α-fluoro-11β-hydroxy-16α,17α-butylidenedioxy-17β-methylsulphinylandrosta-1,4-dien-3-one | 6.6 nM |
| 6α,9α-difluoro-11β-hydroxy-16α,17α-isopropylidenedioxy-17β-methylthioandrosta-,4-dien-3-one | 3.2 nM |
| (20R)-9α-fluoro-11β-hydroxy-16α,17α-(E)-2-butenylidenedioxy-17β-methylthioandrosta-1,4-dien-3-one | 2.6 nM |
| (20R,S)-9α-fluoro-11β-hydroxy-16α,17α-butylidenedioxy-17β-isopropylthioandrosta-1,4-dien-3-one | 5.5 nM |
| (20R,S)-9α-fluoro-11β-hydroxy-16α,17α-butylidenedioxy-17β-ethylthioandrosta-1,4-dien-3-one | 4.1 nM |
| (20R)-9α-fluoro-11β-hydroxy-16α,17α-butylidenedioxy-17β-fluoromethylthioandrosta-1,4-dien-3-one | 7.5 nM |

-continued

| | |
|---|---|
| (20R)-6α,9α-difluoro-11β-hydroxy-16α,17α-butylidene-dioxy-17β-methylthioandrosta-1,4-dien-3-one | 3.7 nM |
| 6α,9α-difluoro-11β-hydroxy-16α,17α-isopropylidenedioxy-17β-fluoromethylthioandrosta-1,4-dien-3-one | 4.1 nM |
| (20R)-6α,9α-difluoro-11β-hydroxy-16α,17α-butylidene-dioxy-17β-fluoromethylthioandrost-4-en-3-one | 3.0 nM |
| (20R)-6α,9α-difluoro-11β-hydroxy-16α,17α-butylidene-fluoromethylthioandrosta-1,4-dien-3-one | 2.7 nM |
| (20S)-6α,9α-difluoro-11β-hydroxy-16α,17α-butylidene-fluoromethylthioandrosta-1,4-dien-3-one | 2.5 nM |
| (20R)-6α,9α-difluoro-11β-hydroxy-16α,17α-butylidene-methylthioandrost-4-en-3-one | 2.9 nM to 3.2 nM |
| (20R)-9α-fluoro-11β-hydroxy-16α,17α-butylidenedioxy-17β-methylthioandrosta-1,4-dien-3,6-dione | 2.4 nM |
| (20R,S)-9α-fluoro-11β-hydroxy-16α,17α-butylidenedioxy-17β-methylthioandrost-4-en-3-one (stereoisomeric ratio 90:10) | 2.5 nM |
| 9α-fluoro-11β-hydroxy-16α,17α-isopropylidenedioxy-17β-(2-pyridylthio)androsta-1,4-dien-3-one | 27 nM |
| (20S)-16α,17α-butylidenedioxy-6α,9α-difluoro-11β-hydroxy-17β-(methylthio)androst-4-ene-3-one | 2.9 nM |
| (20R)-16α,17α-butylidenedioxy-6α,9α-difluoro-11β-hydroxy-(methylthio)androstan-3-one | 2.6 nM |
| (20S)-16α,17α-butylidenedioxy-6α,9α-fluoro-11β-hydroxy-(methylthio)androst-4-en-3,6-dione | 3.4 nM |

Further tests which demonstrate the effectiveness of compounds of this invention are as follows. The following representative compound illustrates the pharmacological activity present with compounds of this invention.

Structure:

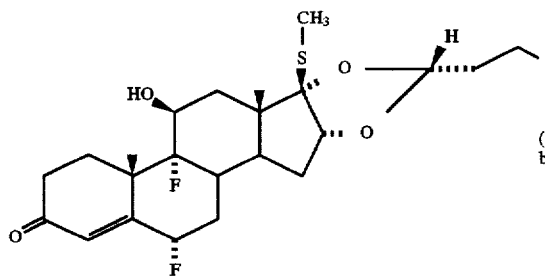

Name:

(20R)-6α,9α-difluoro-11β-hydroxy-16α,17α-butylidenedioxy-17β-methylthioandrosta-4-en-3-one

INHIBITION OF TUMOUR NECROSIS FACTOR (TNF-α) RELEASE FROM HUMAN PERIPHERAL BLOOD MONOCYTES

Monocytes are obtained from blood samples taken from normal human donors. The leukocyte population is washed, applied to a discontinuous metrizamide gradient, and fractionated by centrifugation. The monocyte-enriched interface is aspirated, the cells washed and total and differential counts performed to determine the number of monocytes. Cells are allowed to adhere to 96-well plates for 1 to 2 hours, and thereafter incubated ($8 \times 10^5$ monocytes/well) with the steroid for 18 hours (37° C. in 5% $CO_2$). Cells are challenged with 10 ng/ml lipopolysaccharide for 4 hours and TNF-α is assayed by use of an enzyme-linked immunosorbent assay. TNF-α quantification is performed with goat anti-human TNF-α being used as the coating antibody, rabbit anti-human TNF-α as the second antibody, and goat anti-rabbit IgG horseradish peroxidase as the detection antibody. The $IC_{50}$ is the steroid concentration reducing TNF-α release by 50%. $IC_{50}$=0.25 nM

INDUCTION OF TYROSINE AMINOTRANSFERASE ACTIVITY

Rat liver H4IIE cells are cultured for 4 days until the cells are confluent. The medium is replaced by fresh medium, containing steroid under test (0–100 nM) which is added to triplicate wells. After overnight incubation as above, the medium is removed and the cells are lysed and the extract is equilibrated at 37° C. with α-ketoglutarate and pyridoxal phosphate in phosphate buffer, pH 7.3, in a final volume of 1 ml. Tyrosine aminotransferase activity is initiated by adding tyrosine and incubating at 37° C. for 10 minutes. The reaction is stopped by adding aqueous sodium hydroxide solution (10M). The ultra-violet absorbance of the para-hydroxybenzaldehyde is measured by a plate reader at 340 nm. The maximal absorbance change achieved with the standard (dexamethasone) is used as a reference. The absorbance change for each concentration of steroid under test is calculated as a fraction of the maximal absorption achievable and plotted against steroid concentration. The $ED_{50}$ is determined as the concentration causing an increase in tyrosine aminotransferase activity of 50% of the maximum achievable. $IC_{50}$=0.3 nM

INHIBITION OF RAT LUNG OEDEMA IN-VIVO:

Test compounds are suspended in 1% carboxymethyl-cellulose/0.2% Tween 80 at double the required strength and sonicated to form a suspension. This is administered intratracheally (i.t.) to male rats (Sprague-Dawley strain, 6 in each group, each weighing about 350 g) at 0 hours and 24 hours, with the first dose being co-administered with saline and the second with Sephadex G200 [cross-linked dextran] (10 mg/ml) giving a final Sephadex concentration of 5 mg/ml. I.t. dosing is carried out under halothane anaesthesia (4% in oxygen, at 4 litres/minute for 3 minutes). At 48 hours, the rats are killed, final body weight is recorded, and the lungs and thymus are removed and weighed. The doses reducing the Sephadex-induced oedema and the thymus weight by 30% ($ED_{30}$) are calculated. Airway selectivity is defined as the ratio of thymus involution ($ED_{30}$) and inhibition of lung oedema ($ED_{30}$).

Lung oedema: $ED_{30}$=0.003 mg/kg
Thymus involution: $ED_{30}$=2.2 mg/kg
Airway selectivity: 733.

INHIBITION OF MOUSE EAR OEDEMA IN-VIVO (i) Steroids are dissolved in acetone and administered epicutaneously to the ventral and dorsal surfaces of the right ear pinna of female mice (CD1 strain, 5 in each group, each weighing about 20 g). 18 Hours later, phorbol myristate acetate (PMA, 1.25 μg/ear) in acetone is applied epicutaneously to the right ear. The mice are killed 4 hours later, and a 5 mm disc is punched out of each ear and weighed. The dose reducing PMA-induced oedema by 50% ($ED_{50}$) is determined from linear regression.

Inhibition of PMA-induced mouse ear oedema: $ED_{50}=$ 0.0082 µg/ear (ii) Ovalbumin sensitised mice are challenged with antigen injected into the right ear intradermally under 4% halothane anaesthesia (4% in oxygen, 4 litres/minute for 2 minutes) 18 hours after topical treatment with the steroids [as above in (i)]. The mice are killed 1 hour later, and a 5 mm disc is punched out of each ear, and weighed. The dose reducing the oedema by 50% ($ED_{50}$) is determined as above. Inhibition of antigen-induced mouse ear oedema: $ED_{50}=$ 0.026 µg/ear In view of the results obtained when compounds of the present invention are subjected to the above tests, it can be demonstrated that valuable properties for the relief of inflammation are indicated.

In clinical practice the compounds are administered in a form suitable for the area of the body to be treated. For example, for the treatment of diseases of the respiratory system they are usually administered as aerosols or, preferably, as dry powder formulations, and for the treatment of diseases of the skin they are usually administered as creams, ointments or lotions. Such formulations are prepared by the application or adaptation of known methods such as the following.

PHARMACEUTICAL COMPOSITIONS

For the topical treatment of skin conditions, the steroids may be administered in a conventional pharmaceutical carrier such as creams, ointments, lotions, emulsions, solutions, foams, or the like.

The steroid compounds of this invention may be used for topical treatment of skin conditions, in the range of about 0.0001 to about 5%, preferably about 0.01 to about 2%, by weight of the vehicle.

For the topical treatment of allergy and asthma the steroids may be administered as a dry powder, for example in a single dose inhaler or a multidose inhaler, or as a suspension or a solution in a metered dose aerosol unit or in a nebuliser, with a suitable carrier, or the like. Such devices are well known in the art and standard modes of preparation may be employed or adapted.

Such formulations for inhalation typically contain from about 10 to about 4,000, preferably from about 100 to about 1,600, µg per dose.

Still further, steroids of this invention may be administered in anal or peri-anal formulations, e.g. foams, solutions or suspensions and suppositories. Such formulation techniques are well known in the art.

An example of a formulation as a retention enema for the treatment of ulcerative colitis (this can also be a continuous drip, i.e. a solution formulation) can be found in the specification of U.S. Pat. No. 4,710,495.

Formulation as liposomes may be used as described in the specification of WO 92/13873.

Slow release oral formulations such as formulations for release into the intestine or colon or both, e.g. slow release tablets, may also be employed.

Such oral and anal or peri-anal formulations are typically administered so as to deliver from about 0.1 to about 100, preferably from about 5 to about 50, mg per day.

The following Composition Example illustrates pharmaceutical compositions according to the present invention.

COMPOSITION EXAMPLE 1

(20R)-6α,9α-Difluoro-11β-hydroxy-16α,17α-butylidenedioxy-17β-methylthioandrost-4-en-3-one (1.0 g) (mean particle size 3.5 microns) and lactose (99 g) (mean particle size 72 microns) are blended together for 30 minutes in a mechanical shaker/mixer. The resulting blend is filled, to a fill weight of 25 mg, into No.3 hard gelatine capsules, to give a product suitable for use, for example, with a dry powder inhaler.

We claim:

1. A compound of the formula:

where:

≡ is independently at each of the 1,2-, 4,5- and 6,7-positions, a single or double bond;

$R_1$ is a straight- or branched-chain $C_{1-4}$ alkyl or $C_{2-4}$ alkenyl;

$R_2$ is hydrogen or methyl;

$R_3$ is $C_{1-7}$ alkyl, phenyl, substituted phenyl, heteroaryl, substituted heteroaryl or —$CH_2R$ where R is halo, hydroxy, $C_{1-5}$ alkoxy or $C_{1-10}$ alkanoyloxy;

$R_4$ is hydrogen, halo, hydroxy, keto or $C_{1-3}$ alkoxy when ≡ at the 6,7-position forms a single bond, or hydrogen, halo or $C_{1-3}$ alkoxy when ≡ at the 6,7-position forms a double bond;

$R_5$ is hydrogen or halo;

$R_6$ is hydrogen when ≡ at the 1,2-position forms a single bond or hydrogen or chloro when ≡ at the 1,2-position forms a double bond; and n is 0–2; or a race mate diasteromer thereof.

2. A compound according to claim 1 where:

≡ is a double bond at the 1,2- and 4,5-positions and a single bond at the 6,7-position;

$R_1$ is alkyl or alkenyl;

$R_2$ is hydrogen, or methyl;

$R_3$ is alkyl, haloalkyl or heteroaryl;

$R_4$ is hydrogen, halo, or keto;

$R_5$ is halo;

$R_6$ is hydrogen; and n is 0–2.

3. A compound according to claim 2 where:

≡ is a double bond at the 1,2- and 4,5-positions and a single bond at the 6,7-position;

$R_1$ is methyl, propyl or trans-prop-1-enyl;

$R_2$ is hydrogen, or methyl;

$R_3$ is methyl, isopropyl, fluoromethyl or pyridyl;

$R_4$ is hydrogen, fluoro, or keto;

$R_5$ is fluoro;

$R_6$ is hydrogen; and n is 0–2.

4. A compound according to claim 1 where:

≡ is a double bond at the 4,5-position and single bonds at the 1,2 and 6,7-positions;

$R_1$ is alkyl or alkenyl;

$R_2$ is hydrogen, or methyl;

$R_3$ is alkyl, haloalkyl or heteroaryl;

$R_4$ is hydrogen, halo, or keto;

$R_5$ is halo;

$R_6$ is hydrogen; and n is 0–2.

5. A compound according to claim 4 where:

⎓ is a double bond at the 4,5-position and a single bond at the 1,2-and 6,7-positions;

$R_1$ is methyl, propyl or trans-prop-1-enyl;

$R_2$ is hydrogen, or methyl;

$R_3$ is methyl, fluoromethyl or pyridyl;

$R_4$ is hydrogen, fluoro, or keto;

$R_5$ is fluoro;

$R_6$ is hydrogen; and n is 0–2.

6. A compound according to claim 3 which is

9α-fluoro-11β-hydroxy-16α, 17α-isopropylidenedioxy-17β-(methylthio)androsta-1,4-dien-3-one;

9α-fluoro-11β-hydroxy-16α, 17α-isopropylidenedioxy-17β-(methylsulphonyl)androsta-1,4-dien-3-one;

9α-fluoro-11β-hydroxy-16α, 17α-isopropylidenedioxy-17β-(2-pyridylthio)androsta-1,4-dien-3-one;

6α,9α-difluoro-11β-hydroxy-16α, 17α-isopropylidenedioxy-17β-(methylthio)androsta-1,4-dien-3-one; or 6α,9α-difluoro-11β-hydroxy-16α, 17α-isopropylidenedioxy-17β-(fluoromethylthio)androsta-1,4-dien-3-one.

7. A compound according to claim 3 selected from:

(20R)-16α, 17α-butylidenedioxy-9α-fluoro-11β-hydroxy-17β-(methylthio)androsta-1,4-dien-3-one;

(20R,S)-16α, 17α-butylidenedioxy-9α-fluoro-11β-hydroxy-17β-(2-pyridyl-thio)androsta-1,4-dien-3-one;

(20R)-16α, 17α-butylidenedioxy-9α-fluoro-11β-hydroxy-17β-(methylsulphinyl)androsta-1,4-dien-3-one;

(20R,S)-16α, 17α-butylidenedioxy-9α-fluoro-11β-hydroxy-17β-(isopropylthio)androsta-1,4-dien-3-one;

(20R,S)-16α, 17α-butylidenedioxy-9α-fluoro-11β-hydroxy-17β-methylthioandrosta-1,4-dien-3-one;

(20R)-16α, 17α-butylidenedioxy-9α-fluoro-11β-hydroxy-17β-(fluoromethylthio)androsta-1,4-dien-3-one;

(20R)-16α, 17β-butylidenedioxy-6α,9α-difluoro-11β-hydroxy-17β-(methylthio)androsta-1,4-dien-3-one;

(20R)-16α, 17α-butylidenedioxy-6α,9α-difluoro-11β-hydroxy-17β-(methylsulphinyl)androsta-1,4-dien-3-one;

(20R)-16α, 17α-butylidenedioxy-6α,9α-difluoro-11β-hydroxy-17β-(fluoromethylthio)androsta-1,4-dien-3-one;

(20R)-16α, 17α-butylidenedioxy-6α,9α-difluoro-11β-hydroxy-17β-(methylthio)androsta-1,4-dien-3-one;

(20S)-16α, 17α-butylidenedioxy-6α,9α-difluoro-11β-hydroxy-17β-(methylsulphonyl)androsta-1,4-dien-3-one; and (20R)-16α, 17α-butylidenedioxy-9α-fluoro-11β-hydroxy-17β-(methylthio)androsta-1,4-diene-3,6-dione.

8. A compound according to claim 3 which is (20R)-16α, 17α-|(E) 2-butenylidenedioxy|-9α-fluoro-11β-hydroxy-17β-(methylthio)androsta-1,4-dien-3-one.

9. A compound according to claim 5 selected from:

(20R,S)-16α, 17α-butylidenedioxy-9α-fluoro-11β-hydroxy-17β-(methylthio)androst-4-en-3-one;

(20R)-16α, 17α-butylidenedioxy-6α,9α-difluoro-11β-hydroxy-17β-(fluoromethylthio)androst-4-en-3-one; and (20R)-16α, 17α-butylidenedioxy-9α-fluoro-11β-hydroxy-17β-(methylthio)androst-4-ene-3,6-dione.

10. A compound according to claim 5 which is (20R)-16α, 17α-butylidenedioxy-6α,9α-difluoro-11β-hydroxy-17β-(methylthio)androst-4-en-3-one.

11. A compound according to claim 1 where ⎓ at in the 1,2-, 4,5- and 6,7-positions are all single bonds.

12. A compound according to claim 11 which is (20R)-16α, 17α-butylidenedioxy-6α,9α-difluoro-11β-hydroxy-17β-(methylthio)androstan-3-one.

13. A pharmaceutical composition which comprises a steroid of claim 1 in association with a pharmaceutical carrier or coating.

14. A process for the preparation of a compound according to claim 1 comprising irradiating a compound of the formula

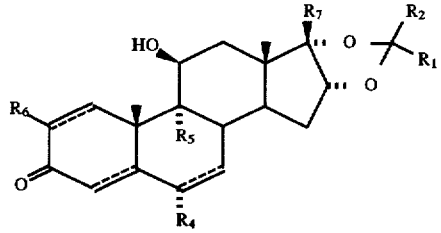

wherein $R_7$ is a 2-thioxo-1,2-dihydropyrid-1-yloxycarbonyl group, in the presence of a compound of the formula $R_3$—S—S(O)$_m$—$R_8$ wherein $R_8$ represents a hydrogen atom or an alkyl group containing up to about 7 carbon atoms, and m represents 0 or 2, under an inert atmosphere.

15. A process for the preparation of a compound according to claim 1 wherein n represents 0, and $R_3$ represents a pyridyl group comprising irradiating a compound of the formula

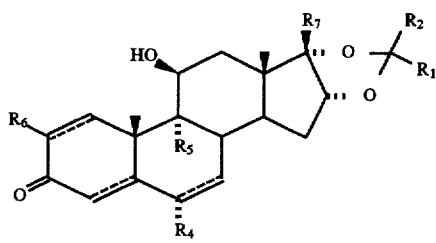

wherein $R_7$ is a 2-thioxo-1,2-dihydropyrid-1-yloxycarbonyl group, under an inert atmosphere.

16. A process for the preparation of a compound according to claim 1 wherein n represents 1 comprising oxidizing a compound according to claim 1 wherein n represents 0.

17. A process for the preparation of a compound according to claim 1 wherein n represents 2 comprising oxidizing a compound according to claim 1 wherein n represents 0 or 1.

18. A process for the preparation of a compound according to claim 1, wherein ═ independently at the 1,2-, 4,5-, and 6,7-positions is a single bond, comprising reducing a compound according to claim 1 wherein ═ independently at the 1,2-, 4,5-, and 6,7-positions is a double bond.

19. A process for the preparation of a compound according to claim 1 wherein n represents 0, and $R_3$ represents a halomethyl group, comprising halogenating a compound according to claim 1 wherein $R_3$ represents a methyl group.

20. A process for the preparation of a compound according to claim 1 wherein $R_4$ represents an alkoxy group, comprising alkylating a compound according to claim 1 wherein $R_4$ represents a hydroxy group.

21. A compound according to claim 1 having (20R)-configuration.

22. A compound according to claim 1 where:

═ is a double bond at the 4,5-position and single bonds at the 1,2-and 6,7-position;

$R_1$ is straight or branched-chain $C_{1-4}$alkyl;

$R_2$ is hydrogen, or methyl;

$R_3$ is $C_{1-7}$alkyl, halomethyl or heteroaryl;

$R_4$ is hydrogen, halo, or keto;

$R_5$ is halo;

$R_6$ is hydrogen; and n is 0–2.

* * * * *

UNITED STATES PATENT AND TRADEMARK OFFICE
CERTIFICATE OF CORRECTION

PATENT NO.    :    5,801,165
DATED         :    September 1, 1998
INVENTOR(S)   :    Michael John Ashton et al.

It is certified that error appears in the above-identified patent and that said Letters Patent is hereby corrected as shown below:

On the title page, item [54] and column 1, line 2:

In the title, replace "ANTIALLERIC" with --ANTIALLERGIC--.

Below "Related U.S. Application Data", replace

"[63]  Continuation of PCT/GB93/02659, Dec. 24, 1992" with
--[63] Continuation-in-part of PCT/GB93/02659, Dec. 24, 1993--.

Signed and Sealed this

Sixteenth Day of March, 1999

Attest:

Q. TODD DICKINSON

Attesting Officer

Acting Commissioner of Patents and Trademarks